US012778643B2

(12) United States Patent
Braal et al.

(10) Patent No.: US 12,778,643 B2
(45) Date of Patent: Nov. 3, 2026

(54) SPINAL IMPLANT SYSTEM AND METHOD

(71) Applicant: Warsaw Orthopedic, Inc., Warsaw, IN (US)

(72) Inventors: Jaredan Braal, Memphis, TN (US); Julien J. Prevost, Memphis, TN (US); Robert M. Loke, Memphis, TN (US); Thomas J. Stinchfield, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 339 days.

(21) Appl. No.: 18/420,903

(22) Filed: Jan. 24, 2024

(65) Prior Publication Data

US 2024/0238016 A1 Jul. 18, 2024

Related U.S. Application Data

(63) Continuation of application No. 16/986,401, filed on Aug. 6, 2020, now Pat. No. 11,911,079.

(51) Int. Cl.

| | |
|---|---|
| ***A61B 17/70*** | (2006.01) |
| ***A61B 34/20*** | (2016.01) |
| ***A61B 34/30*** | (2016.01) |
| *A61B 17/00* | (2006.01) |

(52) U.S. Cl.

CPC .......... *A61B 17/7082* (2013.01); *A61B 34/20* (2016.02); *A61B 34/30* (2016.02); *A61B 2017/00199* (2013.01); *A61B 2034/2046* (2016.02); *A61B 2034/2074* (2016.02)

(58) Field of Classification Search

CPC ............ A61B 17/7074; A61B 17/7076; A61B 17/7082; A61B 17/7058–7059; A61B 34/20; A61B 2034/2046

See application file for complete search history.

(56) References Cited

U.S. PATENT DOCUMENTS

| | | | | |
|---|---|---|---|---|
| 2007/0282341 | A1* | 12/2007 | Hes | A61B 17/863 606/328 |
| 2014/0046445 | A1* | 2/2014 | Brennan | A61B 17/8685 606/279 |
| 2014/0148853 | A1* | 5/2014 | Smith | A61B 17/863 606/246 |
| 2014/0172025 | A1* | 6/2014 | Vaughan | A61B 17/8625 606/309 |
| 2014/0277188 | A1* | 9/2014 | Poulos | B65D 43/0231 606/311 |
| 2016/0051284 | A1* | 2/2016 | Cronen | A61B 17/1757 606/279 |
| 2017/0049485 | A1* | 2/2017 | Meyer | A61B 17/7058 |

* cited by examiner

*Primary Examiner* — Eduardo C Robert
*Assistant Examiner* — Michelle C Green
(74) *Attorney, Agent, or Firm* — Sorell, Lenna & Schmidt, LLP

(57) ABSTRACT

A spinal implant comprises at least one bone fastener including a proximal portion configured for fixation with a first anterior cortical surface of a vertebra and a distal portion configured for fixation with a second cortical surface of the vertebra. The proximal portion is engageable with a surgical driver having a surgical navigation component that generates data for display of an image representing position of the spinal implant relative to the vertebra. The spinal implant can be employed with cervical, thoracic, lumbar and/or sacral regions of a spine. Systems, surgical instruments and methods are disclosed.

20 Claims, 16 Drawing Sheets

SPINAL IMPLANT SYSTEM AND METHOD

CROSS REFERENCE TO RELATED APPLICATIONS

This application is a continuation of U.S. patent application Ser. No. 16/986,401, filed Aug. 6, 2020, which is expressly incorporated by reference herein, in its entirety.

TECHNICAL FIELD

The present disclosure generally relates to medical devices for the treatment of musculoskeletal disorders, and more particularly to a spinal implant system and a method for treating vertebrae.

BACKGROUND

Spinal pathologies and disorders such as degenerative disc disease, disc herniation, spondylolisthesis, stenosis, osteoporosis, tumor, kyphosis, scoliosis and other curvature abnormalities, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, injection, mobilization, rehabilitation and exercise can be effective, however, may fail to relieve the symptoms associated with these disorders. Surgical treatment of these disorders can include the use of implants for fusion and/or fixation to provide stability to a treated region. For example, surgical treatment may employ surgical instruments and implants that are manipulated for fixation with bone to stabilize vertebrae. This disclosure describes an improvement over these prior technologies.

SUMMARY

In one embodiment, a spinal implant is provided. The spinal implant includes at least one bone fastener including a proximal portion configured for fixation with a first anterior cortical surface of a vertebra and a distal portion configured for fixation with a second cortical surface of the vertebra. The proximal portion is engageable with a surgical driver having a surgical navigation component that generates data for display of an image representing position of the spinal implant relative to the vertebra. In some embodiments, the spinal implant can be employed with cervical, thoracic, lumbar and/or sacral regions of a spine. In some embodiments, systems, surgical instruments and methods are disclosed.

In one embodiment, a spinal implant system is provided. The spinal implant system includes a spinal implant including at least one bone fastener. The at least one bone fastener includes a proximal portion configured for fixation with a first cortical surface of a cervical vertebra and a distal portion configured for fixation with a second cortical surface of the cervical vertebra. A surgical driver is engageable with the proximal portion to deliver the at least one bone fastener from an anterior trajectory. The surgical driver includes a surgical navigation component that communicates with a tracking device including a sensor that receives a signal and communicates with a processor to generate data for display of an image from a monitor. The image represents position of the spinal implant relative to the cervical vertebra.

In one embodiment, a method for treating a spine is provided. The method comprises the steps of: selecting a pathway from an anterior approach that includes cervical vertebrae; creating a cavity in a first cortical surface of a cervical vertebra and a cavity in a second cortical surface of the cervical vertebra, the cavities being created along the pathway via surgical navigation; and delivering a spinal implant including at least one bone fastener along the pathway via surgical navigation, the at least one bone fastener including a proximal portion fixable with the first cortical surface and a distal portion fixable with the second cortical surface.

BRIEF DESCRIPTION OF THE DRAWINGS

The present disclosure will become more readily apparent from the specific description accompanied by the following drawings, in which.

DETAILED DESCRIPTION

Figure 1:
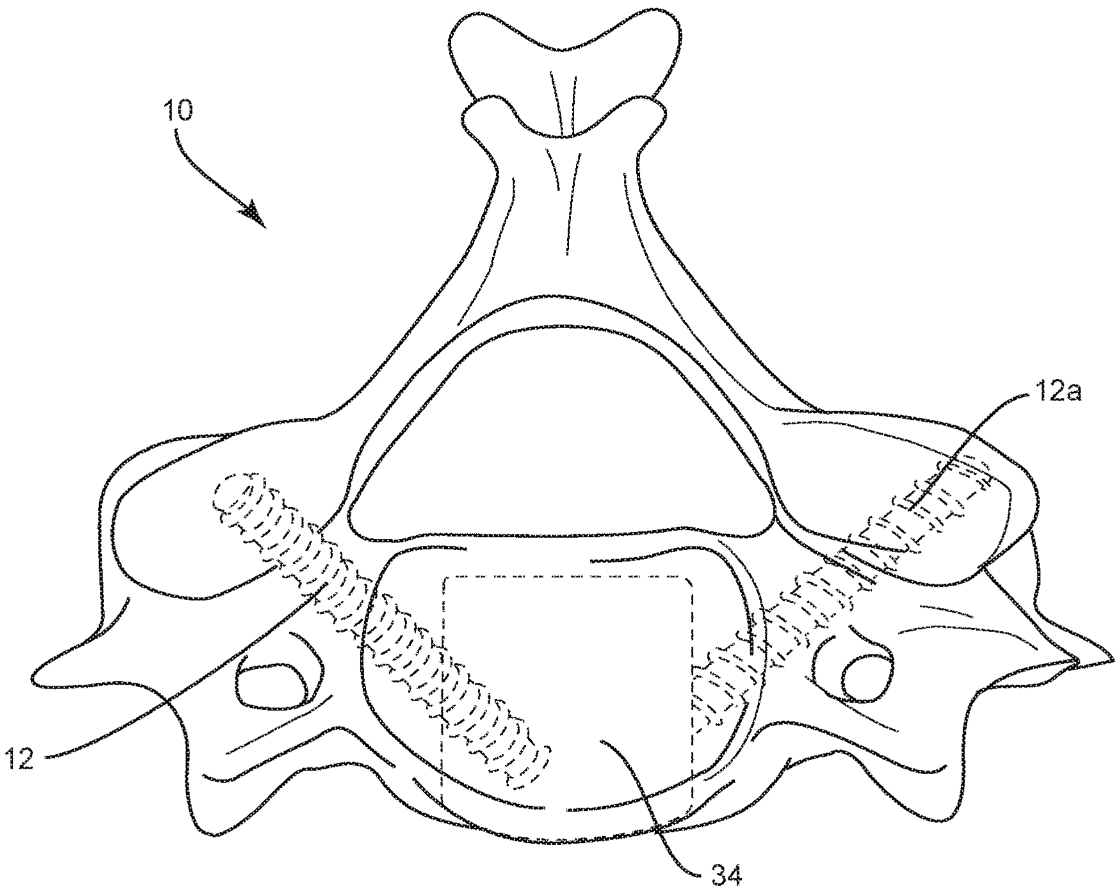
FIG. 1 is a plan view of components of one embodiment of a spinal implant in accordance with the principles of the present disclosure disposed with vertebrae.

The exemplary embodiments of the spinal implant system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, for example, with a cervical, thoracic, lumbar and/or sacral region of a spine. In some embodiments, the present system is employed with a method including a spinal implant, for example, a bone fastener that is implanted anteriorly into a cervical vertebra or cervical vertebrae such that the bone fastener draws the cervical vertebra or cervical vertebrae into fixation to promote fusion.

In some embodiments, the present spinal implant system and method include an anterior cervical discectomy and fusion device including a spinal implant, for example, a bone fastener. In some embodiments, the bone fastener is a pedicle screw. In some embodiments, the bone fastener is implanted anteriorly and a patient maintains a supine position without the need for rotation. In some embodiments, the bone fastener includes a proximal portion configured for fixation with a first anterior cortical surface of a cervical vertebra and a distal portion configured for fixation with a second cortical surface of the cervical vertebra. In some embodiments, the second cortical surface is a pedicle of the cervical vertebra. In some embodiments, the proximal portion is engageable with a surgical driver having a surgical navigation component that generates data for display of an image representing position of the spinal implant relative to the cervical vertebra.

In some embodiments, the present spinal implant system and method include a spinal implant, for example, a bone fastener employed with a surgical navigation component and a navigation software component to prevent the bone fastener from loosening within a cervical vertebra. In some embodiments, the surgical navigation component and/or the navigation software component facilitates a bone fastener trajectory, for example, an anterior trajectory for bone fastener fixation. In some embodiments, an anterior cervical bone fastener trajectory via the surgical navigation component and/or the navigation software component enables a user to employ bone fasteners of various dimensions instead of being limited to the archetypal bone fasteners employed in anterior cervical discectomy and fusion. In some embodiments, anterior cervical bone fastener trajectory enables bi-cortical fixation of the cervical vertebra. In some embodiments, the bone fastener and the surgical navigation component enable a robust fixation with the cervical vertebra thus enabling the screw to be implanted in an anterior trajectory.

In some embodiments, the surgical navigation component and/or the navigation software component are configured to fix an anterior cervical plate or an interbody device with one or more bone fasteners. In some embodiments, the bone fasteners are inserted via an anterior approach into a cervical vertebra and into a pedicle of the vertebra. In some embodiments, the interbody device engages with the bone fasteners and the bone fasteners are configured to move independently relative to the interbody device. In some embodiments, the surgical navigation component and/or the navigation software component enables the bone fasteners to be delivered via an anterior trajectory while also avoiding vertebral arteries. In some embodiments, the present spinal implant system and method provide an anterior approach that reduces morbidity relative to a posterior approach and provides robust fixation of the bone fastener or bone fasteners. In some embodiments, the present spinal implant system and method provide decompression, alignment and stabilization from an anterior approach and avoids a 360 fusion.

In some embodiments, the present spinal implant system and method include a spinal implant, for example, an interbody device, a first bone fastener and a second bone fastener. In some embodiments, the interbody device and the bone fasteners are configured for engagement for fixation with vertebrae, for example, cervical vertebrae. In some embodiments, at least one of the bone fasteners include a threaded proximal portion and a threaded distal portion. In some embodiments, only the proximal and distal portions of the bone fastener are threaded to ensure that sharp threaded edges are not located adjacent to a vertebral artery or arteries. In some embodiments, a non-threaded section is disposed between the threaded proximal and distal portions. In some embodiments, the non-threaded section is disposed adjacent to the vertebral artery or arteries. In some embodiments, at least one of the bone fasteners include a smooth shaft that includes expandable threads that deploy after the bone fastener passes the vertebral artery or arteries. In some embodiments, at least one of the bone fasteners are fully threaded from the proximal portion to the distal portion along a length of the shaft of the bone fastener. In some embodiments, the bone fasteners can be positioned in divergent trajectories. In some embodiments, the bone fasteners can be positioned in convergent trajectories. In some embodiments, the bone fasteners can be positioned in crossing trajectories. In some embodiments, the present spinal implant system and method include a spinal implant, for example, an interbody device and four bone fasteners disposed with one or more vertebral levels.

In some embodiments, the present spinal implant system and method include a spinal implant, for example, an anterior cervical plate and four bone fasteners disposed with one or more vertebral levels. In some embodiments, the present spinal implant system and method reduces instances of pseudoarthrosis and/or a loss of sagittal correction.

In some embodiments, the present spinal implant system and method include a spinal implant, for example, a bone fastener that is fixed to a cervical vertebra from an anterior trajectory for bi-cortical fixation. In some embodiments, the bi-cortical fixation of the bone fastener obviates the need for additional bone fasteners and/or rods due to fixation in cortical bone being more stable due to the strength of the cortical bone.

In some embodiments, the present spinal implant system and method include a spinal implant, for example, a bone fastener that includes a proximal portion including a first head, and a distal portion. A shaft extends between the proximal portion and the distal portion. In some embodiments, a second head is manually engaged at the distal portion. In some embodiments, the distal portion is manually engaged in a pop-on or snap-on engagement with the second head. In some embodiments, the bone fastener traverses an entire vertebral body and out through a pedicle such that the pop-on or snap-on head is attached, thereby providing a single anterior and posterior construct. In some embodiments, the head includes a multi axial screw (MAS) head. In some embodiments, the pop-on or snap-on head will protrude from the distal portion of the bone fastener. In some embodiments, the bone fastener and pop-on or snap-on head eliminates the need for additional bone fasteners that would crowd the vertebra and also facilitates robust fixation in weak bone for posterior correction. In some embodiments, the bone fastener and pop-on or snap-on head can be combined with posterior rods to facilitate additional stabilization and would allow for posterior correction. In some embodiments, the bone fastener includes one or more fenestrations. In some embodiments, cement can be implemented with the bone fastener.

In some embodiments, the present spinal implant system is employed with a method for treating a spine. In some embodiments, the method includes the step of selecting a pathway from an anterior approach that includes cervical vertebrae. In some embodiments, the method includes the step of creating a cavity in a first cortical surface of a cervical vertebra and a cavity in a second cortical surface of the cervical vertebra, the cavities being created along the pathway via surgical navigation. In some embodiments, the method includes the step of delivering a spinal implant including at least one bone fastener along the pathway via surgical navigation, the at least one bone fastener including a proximal portion fixable with the first cortical surface and a distal portion fixable with the second cortical surface.

In some embodiments, the present spinal implant system is employed with a method of anterior cervical disc fixation with a robotically guided spinal implant, for example, a bone fastener. In some embodiments, the method includes percutaneous robotically guided implantation of one or more bone fasteners. In some embodiments, the present spinal implant system and method comprise a surgical instrument that includes a spinal implant driver guidable through an end effector of a robotic arm for spinal implant, for example, bone fastener insertion. In some embodiments, the spinal implant driver is configured to rotate within an inside diameter of a robotic arm guide without becoming disengaged therefrom.

In some embodiments, the present spinal implant system and method comprise a surgical instrument that comprises a screw driver that can be employed with spinal implants, such as bone fasteners and/or one or more implant supports for treating a spine. In some embodiments, the present spinal implant system and method include a surgical instrument that can easily connect and disconnect from a spinal implant. In some embodiments, the present spinal implant system and method include a surgical instrument that can be employed with an end effector of a robotic arm to facilitate implantation with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the present spinal implant system is employed with a method used with surgical navigation, for example, fluoroscopic or image guidance. In some embodiments, the presently disclosed system and/or method reduce operating time for a surgical procedure and reduce radiation exposure due to fluoroscope or image guidance, for example, by eliminating procedural steps and patient repositioning by implanting system components in one body position.

In some embodiments, the spinal implant system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the spinal implant system of the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The spinal implant system of the present disclosure may also be alternatively employed with procedures for treating the cervical, lumbar, thoracic, sacral and pelvic regions of a spinal column. The spinal implant system of the present disclosure may also be used on animals, bone models and other non-living substrates, for example, in training, testing and demonstration.

The spinal implant system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms “a,” “an,” and “the” include the plural, and reference to a particular numerical value includes at least that particular value, unless the context clearly dictates otherwise. Ranges may be expressed herein as from “about” or “approximately” one particular value and/or to “about” or “approximately” another particular value. When such a range is expressed, another embodiment includes from the one particular value and/or to the other particular value. Similarly, when values are expressed as approximations, by use of the antecedent “about,” it will be understood that the particular value forms another embodiment. It is also understood that all spatial references, for example, horizontal, vertical, top, upper, lower, bottom, left and right, are for illustrative purposes only and can be varied within the scope of the disclosure. For example, the references “upper” and “lower” are relative and used only in the context to the other, and are not necessarily “superior” and “inferior”.

As used in the specification and including the appended claims, “treating” or “treatment” of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a spinal implant system including a spinal implant, related components and methods of employing the spinal implant system in accordance with the principles of the present disclosure. Alternate embodiments are also disclosed. Reference is made in detail to the exemplary embodiments of the present disclosure, which are illustrated in the accompanying figures. Turning to FIGS. 1-7, there are illustrated components of a surgical system, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant at a surgical site of a patient, for example, regions of a spine including vertebrae, for example cervical vertebrae, and/or articular surfaces of a vertebral joint. In some embodiments, the components of spinal implant system 10 are employed to stabilize and maintain structural integrity of one or more cervical vertebra. In some embodiments, spinal implant system 10 is configured for treating cervical vertebral disorders including those caused by degeneration or trauma. In some embodiments, spinal implant system 10 can include one or more components of one or more spinal constructs, for example, bone fasteners, interbody devices, interbody cages, spinal rods, tethers, connectors, plates and/or bone graft, and can be employed with various surgical procedures including surgical treatment of a cervical, thoracic, lumbar and/or sacral region of a spine, and/or iliac bone.

Spinal implant system 10 includes a spinal implant, for example, bone fastener 12, as shown in FIG. 1. Bone fastener 12 is configured to facilitate treatment of disorders including those caused by degeneration or trauma. For example, bone fastener 12 is configured for implantation with one or more cervical vertebra from an anterior trajectory for anterior cervical discectomy and fusion.

Bone fastener 12 includes a shaft 28 having a proximal portion 14 and a distal portion 16. Portion 14 is configured for fixation with vertebral tissue, for example, a cortical anterior surface CAS of a cervical vertebra V1 via an opening, for example, cavity 18, as shown in FIGS. 4-7. Shaft 28 includes an outer surface 20. Surface 20 includes a uniform, threaded surface configuration that is fully threaded from portion 14 to distal portion 16 along a length of shaft 28. In some embodiments, all or only a portion of shaft 28 may have alternate cross section configurations, such as, for example, oval, oblong, triangular, square, polygonal, irregular, uniform, non-uniform, offset, staggered, undulating, arcuate, variable and/or tapered. In some embodiments, all or only a portion of shaft 28 may have alternate surface configurations to enhance fixation with tissue such as, for example, rough, arcuate, undulating, mesh, porous, semi-porous, dimpled and/or textured. In some embodiments, all or only a portion of shaft 28 may be disposed at alternate orientations, relative to its longitudinal axis, such as, for example, transverse, perpendicular and/or other angular orientations such as acute or obtuse, co-axial and/or may be offset or staggered. In some embodiments, shaft 28 may include one or a plurality of openings. In some embodiments, all or only a portion of bone fastener 12 may be cannulated. In some embodiments, shaft 28 is surface treated with for example, HA.

In some embodiments, surface 20 may include one thread form configuration or a plurality of different thread form configurations. In some embodiments, the thread form configurations may include a single thread turn or a plurality of discrete threads. In some embodiments, other engaging structures may be located along surface 20, in place of or in addition to the thread form configurations discussed above, for example, a nail configuration, barbs, expanding elements, raised elements and/or spikes to facilitate engagement with tissue, for example, one or more cervical vertebra.

Figure 2:
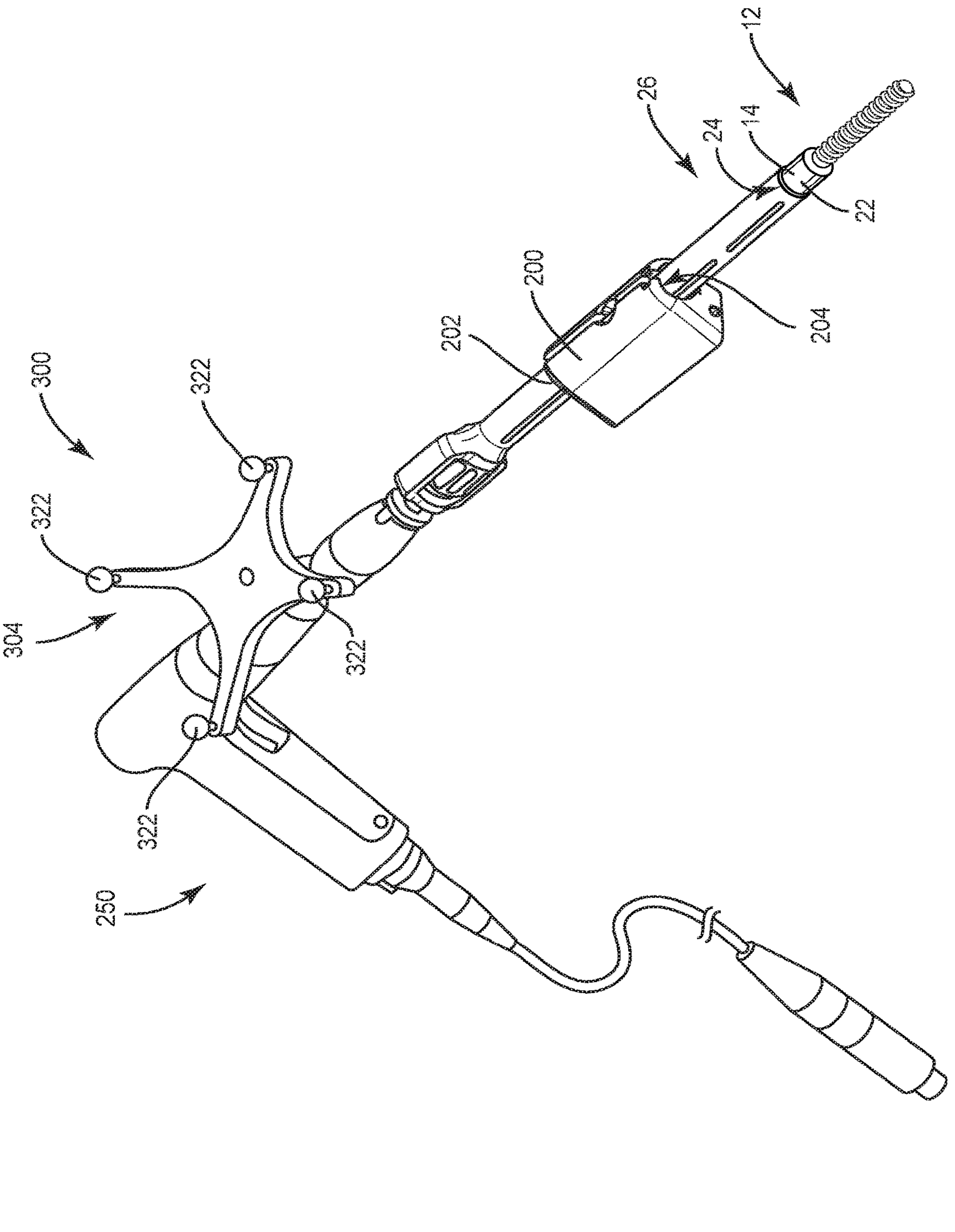
FIG. 2 is a perspective view of components of one embodiment of a spinal implant system in accordance with the principles of the present disclosure.

Portion 14 includes a head 22 that defines a socket 24 for engagement with a surgical driver 26, as shown in FIG. 2, to insert bone fastener 12 into cortical anterior surface CAS of vertebrae V1, as described herein. In some embodiments, socket 24 has a hexalobe configuration. In some embodiments, socket 24 can include a circular, cruciform, phillips, square, polygonal, or star cross sectional configuration. In some embodiments, head 22 may be variously configured and dimensioned, for example, oval, oblong, square, rectangular, polygonal, irregular, uniform, non-uniform, offset, staggered, tapered, consistent or variable.

Figure 4:
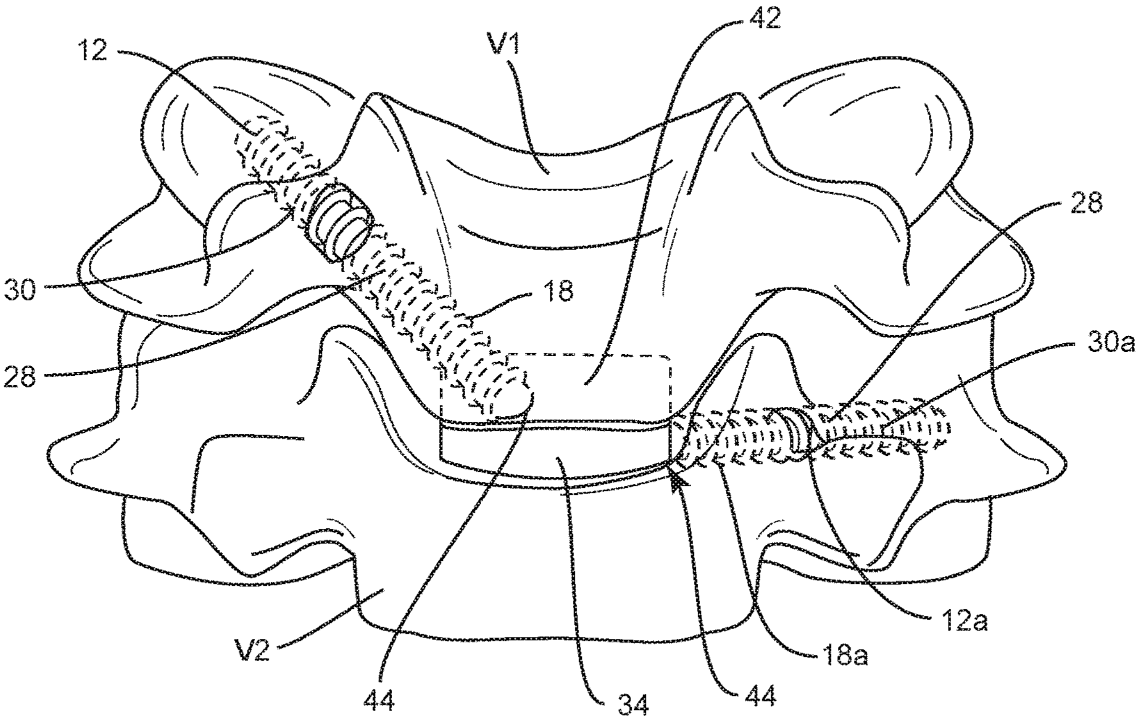
FIG. 4 is a plan view of components of one embodiment of a spinal implant in accordance with the principles of the present disclosure disposed with vertebrae.
Figure 5:
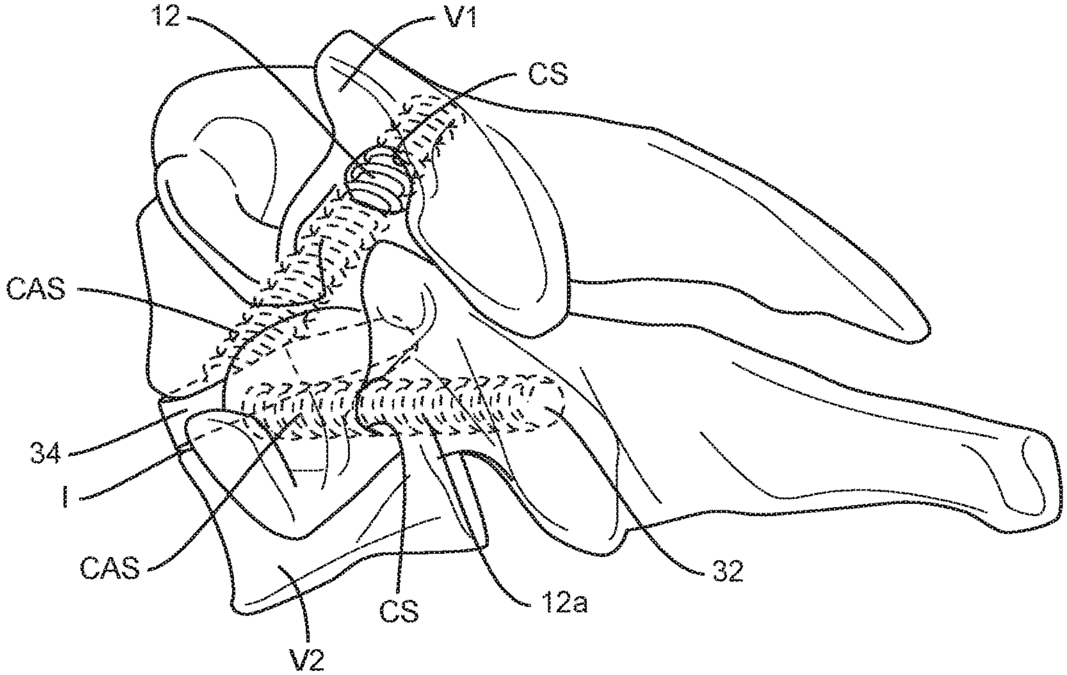
FIG. 5 is a side view of the components and vertebrae shown in FIG. 4.

Portion 16 is configured for fixation with a cortical surface CS, for example, a pedicle of vertebra V1 via an opening, for example, cavity 30, as shown in FIGS. 4 and 5. Cortical anterior surface CAS is spaced apart from cortical surface CS such that bone fastener 12 is engaged with tissue for bi-cortical fixation with vertebra V1, as shown in FIG. 4.

Portion 16 includes a tip 32 to facilitate penetration of cortical bone tissue and/or cancellous bone. In some embodiments, tip 32 can be tapered and/or have a blunt configuration. In some embodiments, tip 32 can include other penetrating elements for example, a nail configuration, barbs, expanding elements, raised elements, ribs, and/or spikes to facilitate engagement of tip 32 with tissue.

As shown in FIGS. 1 and 4-7, the spinal implant includes bone fastener 12 and a bone fastener 12*a*, similar to bone fastener 12. Bone fastener 12 is configured for fixation with cervical vertebra V1 and bone fastener 12*a* is configured for fixation with a cervical vertebra V2. In some embodiments, vertebra V1 is disposed in an orientation with the spine or section of vertebrae as a cephalad vertebra and vertebra V2 is disposed in an orientation with the spine or section of vertebrae as a caudal vertebra. In some embodiments, bone fasteners 12, 12*a* are configured for delivery and/or fixation with vertebral tissue via a divergent trajectory. In some embodiments, bone fasteners 12, 12*a* are configured for delivery and/or fixation with vertebral tissue via a convergent trajectory. In some embodiments, bone fasteners 12, 12*a* are configured for delivery and/or fixation with vertebral tissue via a crossing trajectory.

Figure 6:
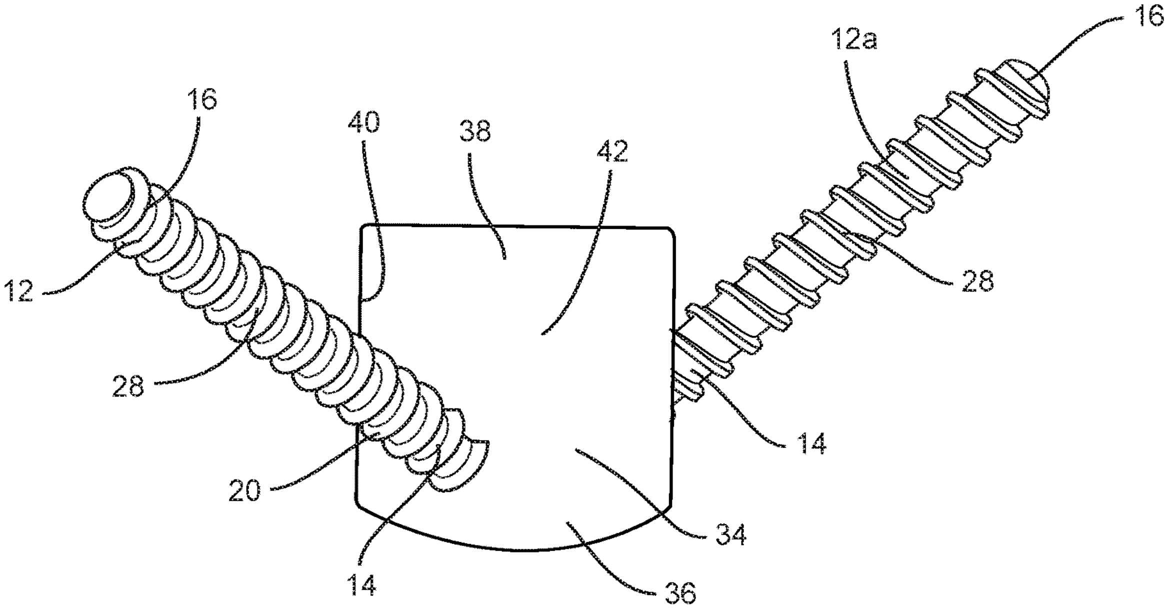
FIG. 6 is a plan view of the components shown in FIG. 4.
Figure 7:
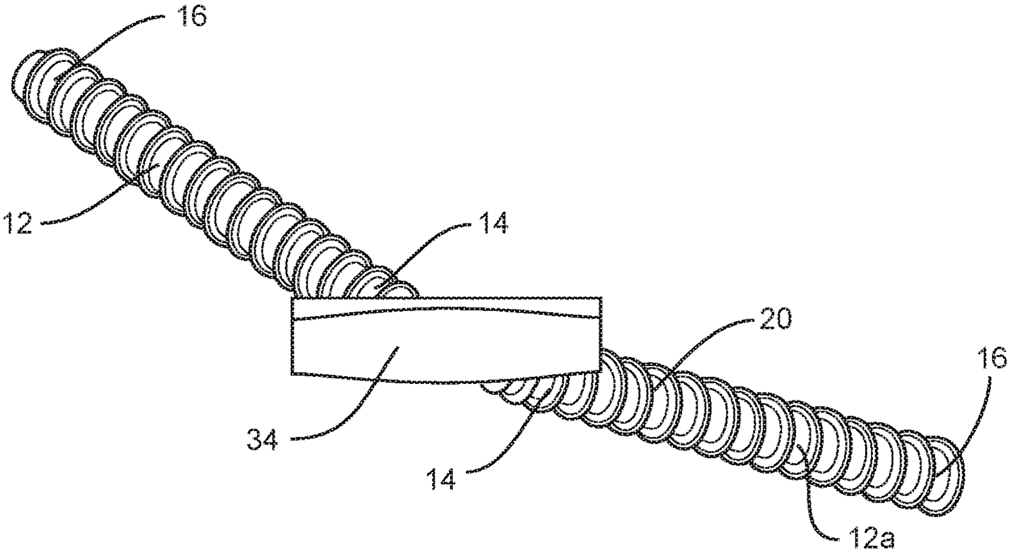
FIG. 7 is a side view of the components shown in FIG. 4.
Figure 8:
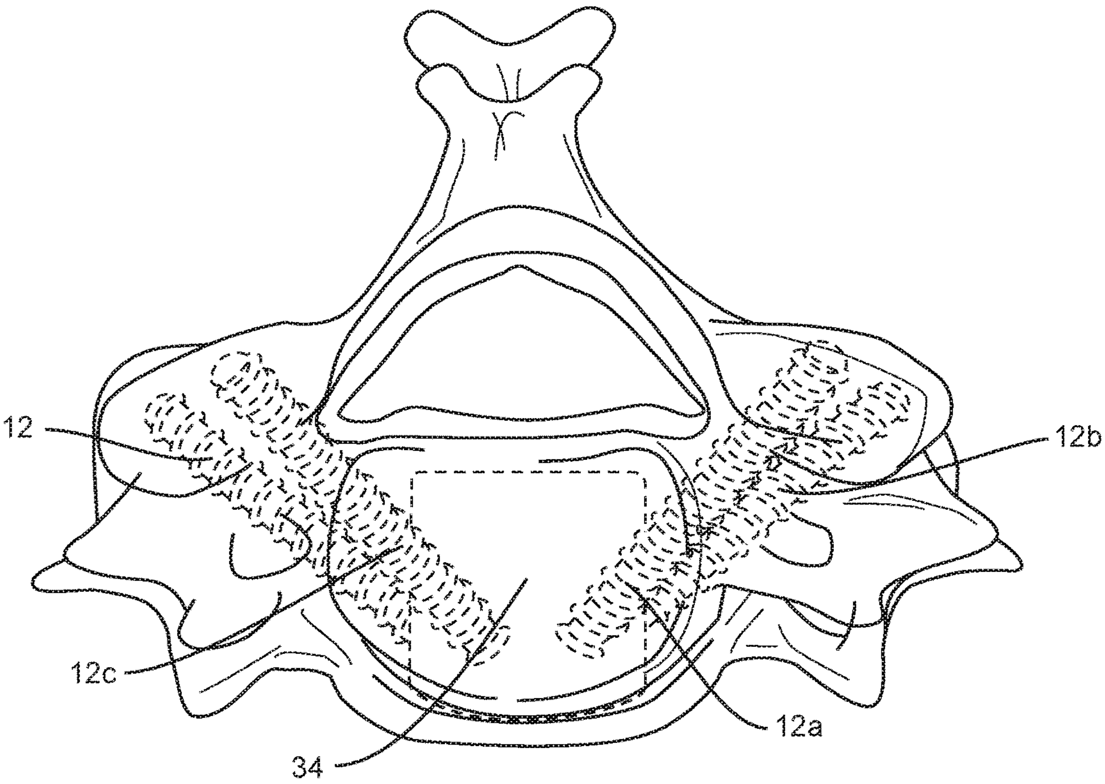
FIG. 8 is a plan view of components of one embodiment of a spinal implant in accordance with the principles of the present disclosure disposed with vertebrae.

Bone fasteners 12, 12*a* are configured for relatively movable disposal with an interbody device 34, as shown in FIGS. 6 and 7. Interbody device 34 is configured for engagement with bone fasteners 12, 12*a* and vertebra V1 and/or vertebra V2. In some embodiments, interbody device 34 is configured to be inserted between vertebra V1 and vertebra V2 within an intervertebral disc space to bear a portion of a load applied to the selected vertebrae. In some embodiments, interbody device 34 includes, an autograft, allograft or other interbody fusion components. Interbody device 34 extends between an end surface 36 and an end surface 38. Interbody device 34 includes a wall 40 that extends between surfaces 36, 38. Interbody device 34 has a surface 42 configured for engagement with vertebrae V1 and V2. In some embodiments, surface 42 may have various surface configurations, such as, for example, rough, threaded, arcuate, undulating, porous, semi-porous, dimpled, polished and/or textured.

Surface 42 defines openings 44 configured for disposal of bone fasteners 12, 12*a*, as shown in FIG. 4. Openings 44 are circular. In some embodiments, openings 44 may be disposed at alternate orientations, relative to wall 40 and/or surface 42, such as, for example, substantially transverse, perpendicular, parallel and/or other angular orientations such as acute or obtuse, and/or may be offset. In some embodiments, openings 44 can be variously configured, such as, for example, oval, oblong, triangular, square, polygonal, irregular, uniform, non-uniform, tapered and/or countersunk. In some embodiments, interbody device 34 can have one or a plurality of openings 44.

Figure 3:
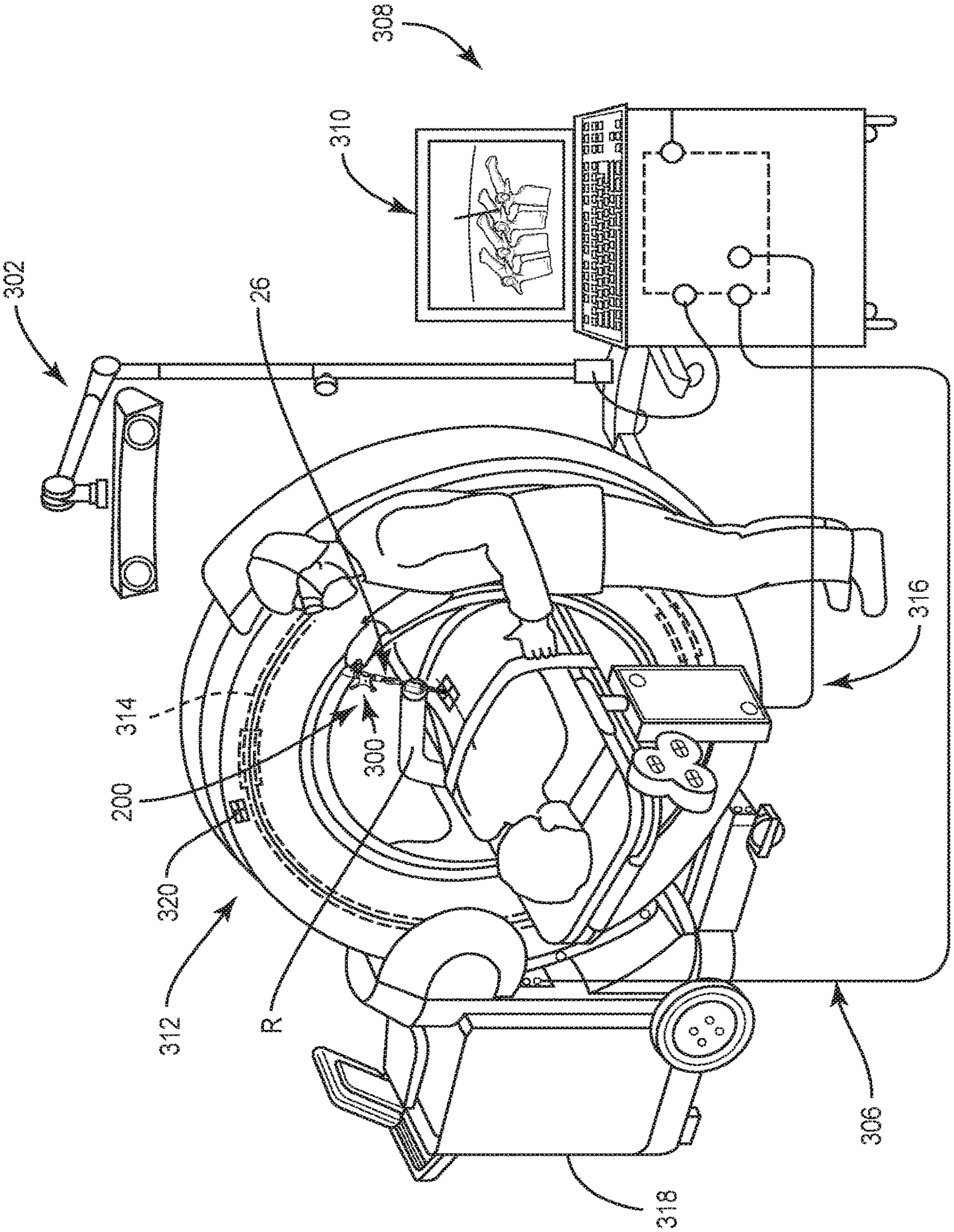
FIG. 3 is a perspective view of components of one embodiment of a spinal implant system in accordance with the principles of the present disclosure.

Driver 26 is engageable with portion 14, for example, via socket 24. Driver 26 is configured for connection with a guide member, for example, an end effector 200 of a robotic arm R, as shown in FIGS. 2 and 3. Driver 26 is guided through end effector 200 for guide-wireless insertion of bone fastener 12 from an anterior trajectory. End effector 200 includes an inner surface 202 that defines a cavity, for example, a channel 204, as shown in FIG. 2. Channel 204 is configured for passage of bone fastener 12 and disposal of driver 26. Robotic arm R includes position sensors (not shown), similar to those referenced herein, which measure, sample, capture and/or identify positional data points of end effector 200 in three dimensional space for a guide-wireless insertion of bone fastener(s) 12 with tissue. In some embodiments, the position sensors of robotic arm R are employed in connection with a surgical navigation system 306, as shown in FIG. 3, to measure, sample, capture and/or identify positional data points of end effector 200 in connection with surgical treatment, as described herein. The position sensors are mounted with robotic arm R and calibrated to measure positional data points of end effector 200 in three-dimensional space, which are communicated to a computer 308.

In some embodiments, driver 26 includes a navigation component 300, as shown in FIG. 2. Driver 26 is configured for disposal adjacent a surgical site such that navigation component 300 is oriented relative to a sensor array 302 to facilitate communication between navigation component 300 and sensor array 302 during a surgical procedure, as described herein. Navigation component 300 is configured to generate a signal representative of a position of bone fastener 12 relative to driver 26 and/or tissue, for example, cortical surfaces of vertebra V1 and/or vertebra V2. In some embodiments, driver 26 can include an image guide such as human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. Navigation component 300 is directly connected to an actuator 250, for example, a powered drill, hand drill or other tool, as shown in FIG. 2. In some embodiments, navigation component 300 is connected with driver 26 via an integral connection, friction fit, pressure fit, interlocking engagement, mating engagement, dovetail connection, clips, barbs, tongue in groove, threaded, magnetic, key/keyslot and/or drill chuck.

Navigation component 300 includes an emitter array 304. Emitter array 304 is configured for generating a signal to sensor array 302 of surgical navigation system 306, as shown in FIG. 3 and described herein. In some embodiments, the signal generated by emitter array 304 represents a position of bone fastener 12 relative to driver 26 and relative to tissue, for example, cortical surfaces of vertebra V1 and/or V2. In some embodiments, the signal generated by emitter array 304 represents a three-dimensional position of bone fastener 12 relative to an anterior surface of vertebra V1 and/or vertebra V2.

In some embodiments, sensor array 302 receives signals from emitter array 304 to provide a three-dimensional spatial position and/or a trajectory of bone fastener 12 relative to driver 26 and/or vertebra V1 and/or vertebra V2. Emitter array 304 communicates with a processor of computer 308 of surgical navigation system 306 to generate data for display of an image on a monitor 310, as described herein. In some embodiments, sensor array 302 receives signals from emitter array 304 to provide a visual representation of a position of bone fastener 12 relative to driver 26 and/or vertebra V1 and/or vertebra V2. See, for example, similar surgical navigation components and their use as described in U.S. Pat. Nos. 6,021,343, 6,725,080, 6,796,988, the entire contents of each of these references being incorporated by reference herein.

Surgical navigation system 306 is configured for acquiring and displaying medical imaging, for example, x-ray images appropriate for a given surgical procedure. In some embodiments, pre-acquired images of a patient are collected. In some embodiments, surgical navigation system 306 can include an O-Arm® imaging device 312 sold by Medtronic Navigation, Inc. having a place of business in Louisville, Colo., USA. Imaging device 312 may have a generally annular gantry housing that encloses an image capturing portion 314.

In some embodiments, image capturing portion 314 may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, for example, an optical tracking system that includes an optical localizer, for example, sensor array 302 and/or an EM tracking system that can include an EM localizer. Various tracking devices can be tracked with tracking system 316 and the information can be used by surgical navigation system 306 to allow for a display of a position of an item, for example, a patient tracking device, an imaging device tracking device 320, and an instrument tracking device, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer 318 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 12 relative to driver 26 and/or tissue for example, cortical surfaces of vertebra V1 and vertebra V2 can be tracked. Sensor array 302 is located in such a manner to provide a clear line of sight with emitter array 304, as described herein. In some embodiments, fiducial markers 322 of emitter array 304 communicate with sensor array 302 via infrared technology. Sensor array 302 is coupled to computer 308, which may be programmed with software modules that analyze signals transmitted by sensor array 302 to determine the position of each object in a detector space.

In assembly, operation and use, spinal implant system 10, similar to the systems and methods described herein, is employed with a surgical procedure, for example, a treatment of an applicable condition or injury of an affected section of a spinal column and adjacent areas within a body. In some embodiments, spinal implant system 10 is employed with a surgical procedure for treatment of one or more cervical vertebra, for example, cervical vertebrae V1 and V2, as shown in FIGS. 4 and 5. In some embodiments, one or all of the components of spinal implant system 10 can be delivered or utilized as a pre-assembled device or can be assembled in situ. Spinal implant system 10 may be completely or partially revised, removed or replaced.

In use, to treat the cervical vertebrae of a patient, a medical practitioner obtains access to a surgical site including vertebrae V1 and V2 in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V1 and V2 are accessed through a mini-incision, or a sleeve that provides a protected passageway to the area. Once access to the surgical site is obtained, the selected surgical procedure can be performed for treating the spine disorder.

An incision is made in the body of a patient and a cutting instrument (not shown) creates a selected surgical pathway, for example, an anterior surgical pathway and/or a surgical pathway disposed along an anterior trajectory oriented relative to the patient body for implantation of components of spinal implant system 10. A speculum (not shown) can be employed to assist in creating the surgical pathway. Tissue can be spaced with a retractor (not shown). A preparation instrument (not shown) can be employed to prepare tissue surfaces of vertebrae V1, V2 and adjacent, as well as for aspiration and irrigation of a surgical region.

In some embodiments, a discectomy is performed. In some embodiments, interbody device 34 is implanted with space I, as shown in FIG. 5. In some embodiments, interbody device 34 may include, for example, autograft, allograft or other interbody fusion device components.

An opening, for example, cavity 18 is created anteriorly in the anterior cortical surface CAS of vertebra V1 along the surgical pathway from an anterior approach to the vertebrae. An opening, for example, cavity 30 is created in the cortical surface CS of vertebra V1 along the surgical pathway. Cavities 18 and 30 can include pilot holes that are formed with a drill (not shown) in the selected areas. In some embodiments, a selected surgical pathway includes an anterior trajectory that passes through a first cortical surface or layer, for example, the CAS of vertebra V1 where the disc has been removed by the discectomy. The surgical pathway then passes through cancellous bone of vertebra V1 and into or through a second cortical surface or layer, for example, the CS of vertebra V1 and/or a pedicle of vertebra V1.

Driver 26 is engaged with socket 24 of bone fastener 12, as shown in FIG. 2. Driver 26 is oriented for disposal with end effector 200 of robotic arm R. The assembly of driver 26/bone fastener 12 is disposed with channel 204 for delivery/implantation of bone fastener 12 with interbody device 34 and cavities 18 and 30 of V1 for bi-cortical fixation by employing robotic arm R and/or surgical navigation system 306. Actuator 250 is connected with driver 26, as described herein, and driver 26 is utilized to drive, torque, insert or otherwise connect bone fastener 12 with V1, as shown in FIG. 4. For example, bone fastener 12 is inserted into cavity 18 formed anteriorly within cortical anterior surface CAS of V1 and threaded surface 20 at portion 14 of bone fastener 12 fixes with the tissue surfaces that define cavity 18. Bone fastener 12 translates through the cancellous bone of V1, as shown in FIG. 5. As portion 14 fixes with the tissue surfaces that define cavity 18, portion 16 is inserted into cavity 30 formed within cortical surface CS of V1, for example, the pedicle, and threaded surface 20 at portion 16 fixes with the tissue surfaces that define cavity 30. In some embodiments, bone fastener 12 passes through an anterior trajectory that passes through a first cortical surface or layer, for example, the CAS of vertebra V1 where the disc has been removed by the discectomy. Bone fastener 12 then passes through cancellous bone of vertebra V1 and into or through a second cortical surface or layer, for example, the CS of vertebra V1 and/or a pedicle of vertebra V1. In some embodiments, bone fastener 12 will stop within the pedicle or pass through a posterior cortical surface and/or layer of vertebra V1.

Sensor array 302 receives signals from navigation component 300 to provide a three-dimensional spatial position and/or a trajectory of the assembly of driver 26/bone fastener 12, which may be disposed with end effector 200, relative to V1 and/or components of spinal implant system 10 for display on monitor 310. Driver 26 is manipulated to disengage with and translate away from bone fastener 12.

Driver 26 is engaged with socket 24 of bone fastener 12*a*. Driver 26 is oriented for disposal with end effector 200 of robotic arm R. The assembly of driver 26/bone fastener 12*a* is disposed with channel 204 for delivery/implantation of bone fastener 12*a* with cavities 18*a* and 30*a* of V2 for bi-cortical fixation by employing robotic arm R and/or surgical navigation system 306. Actuator 250 is connected with driver 26, as described herein, and driver 26 is utilized to drive, torque, insert or otherwise connect bone fastener 12*a* with V2, as shown in FIG. 4. For example, bone fastener 12*a* is inserted into cavity 18*a* formed anteriorly within cortical anterior surface CAS of V2 and threaded surface 20 at portion 14 of bone fastener 12*a* fixes with the tissue surfaces that define cavity 18*a*, as shown in FIG. 4. Bone fastener 12*a* translates through the cancellous bone of V2, as shown in FIG. 5. As portion 14 fixes with the tissue surfaces that define cavity 18*a*, portion 16 is inserted into cavity 30*a* formed within cortical surface CS of V2, for example, the pedicle, and threaded surface 20 at portion 16 fixes with the tissue surfaces that define cavity 30*a*.

Sensor array 302 receives signals from navigation component 300 to provide a three-dimensional spatial position and/or a trajectory of the assembly of driver 26/bone fastener 12*a*, which may be disposed with end effector 200, relative to V2 and/or components of spinal implant system 10 for display on monitor 310. Driver 26 is manipulated to disengage with and translate away from bone fastener 12*a*.

Upon completion of a procedure, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

Figure 9:
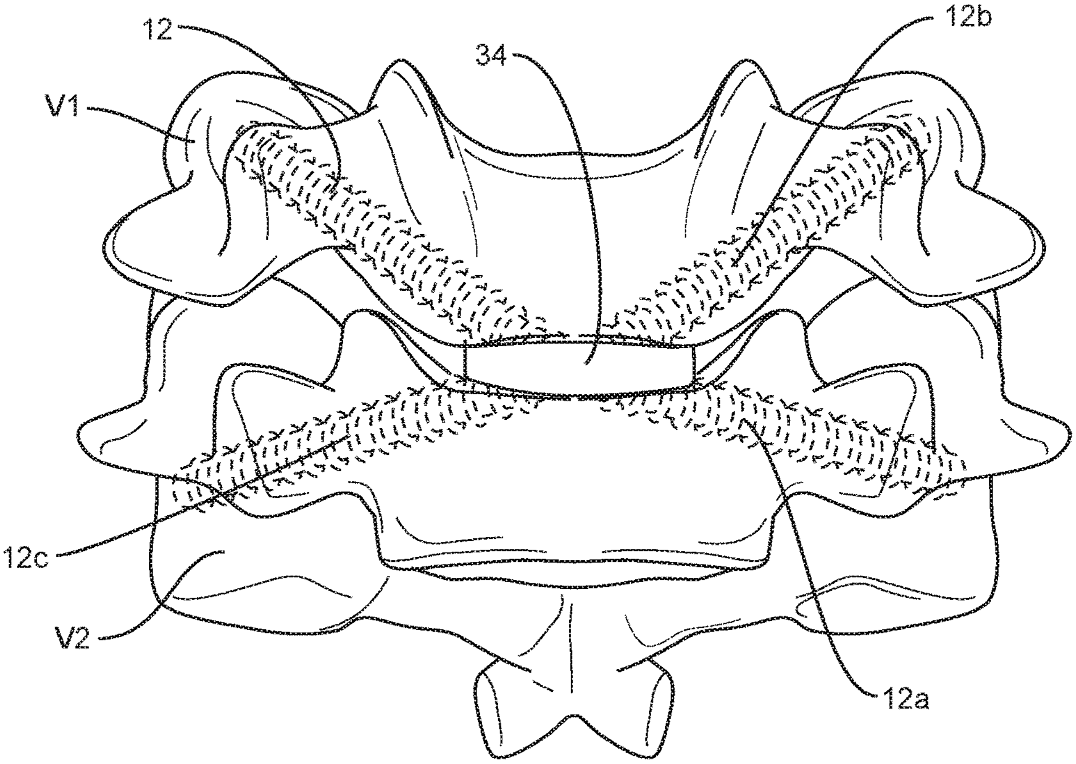
FIG. 9 is a side view of the components shown in FIG. 8.
Figure 10:
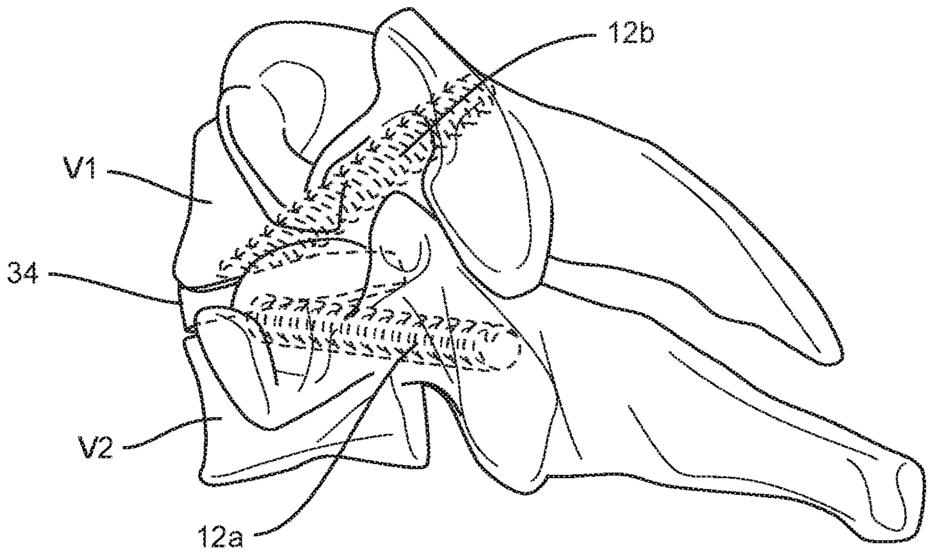
FIG. 10 is a side view of the components and vertebrae shown in FIG. 8.
Figure 11:
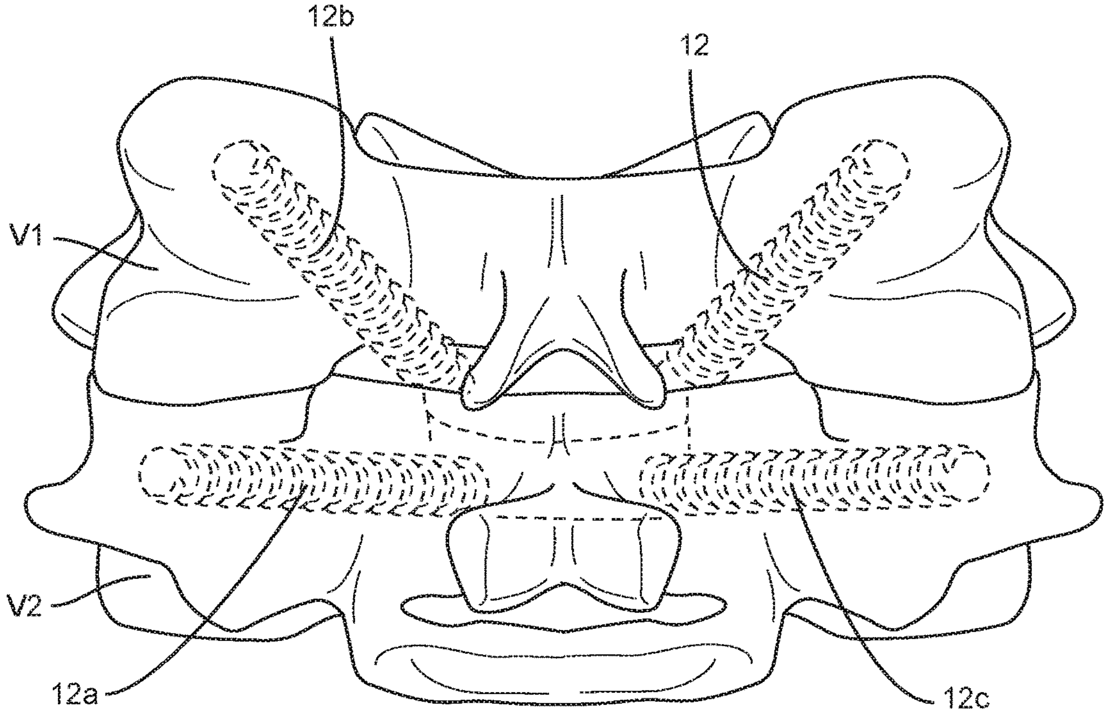
FIG. 11 is a plan view of the components and vertebrae shown in FIG. 8.

In one embodiment, as shown in FIGS. 8-11, spinal implant system 10, similar to the systems and methods described with regard to FIGS. 1-7, includes bone fasteners 12, 12*a*, and bone fasteners 12*b* and 12*c* similar to bone fastener 12. Bone fasteners 12, 12*a*, 12*b* and 12*c* are configured for engagement with openings 44 of interbody device 34. Bone fasteners 12, 12*b* are configured for fixation with vertebra V1 and bone fasteners 12*a*, 12*c* are configured for fixation with vertebra V2, as shown in FIG. 9.

In one embodiment, as shown in FIGS. 12-15, spinal implant system 10, similar to the systems and methods described with regard to FIGS. 1-7, includes bone fastener 120, similar to bone fastener 12. Bone fastener 120 includes a shaft 123 having a proximal portion 122 and a distal portion 124. Shaft 123 includes an outer surface 126. Surface 126 is threaded at portions 122, 124 and has a smooth surface configuration at an intermediate portion 125 disposed therebetween. Surface 126 is threaded only at portions 122, 124 to prevent threaded edges from being positioned, disposed and/or oriented adjacent to tissue, for example, a vertebral artery or arteries to prevent damaging tissue. Portions 122, 124 are configured for fixation with the cortical surfaces of vertebrae V1, as described herein, and portion 125 is disposed with cancellous bone of V1. In some embodiments, intermediate portion 125 is smooth and includes expandable threads that deploy after bone fastener 120 passes the vertebral artery or arteries.

Figure 12:
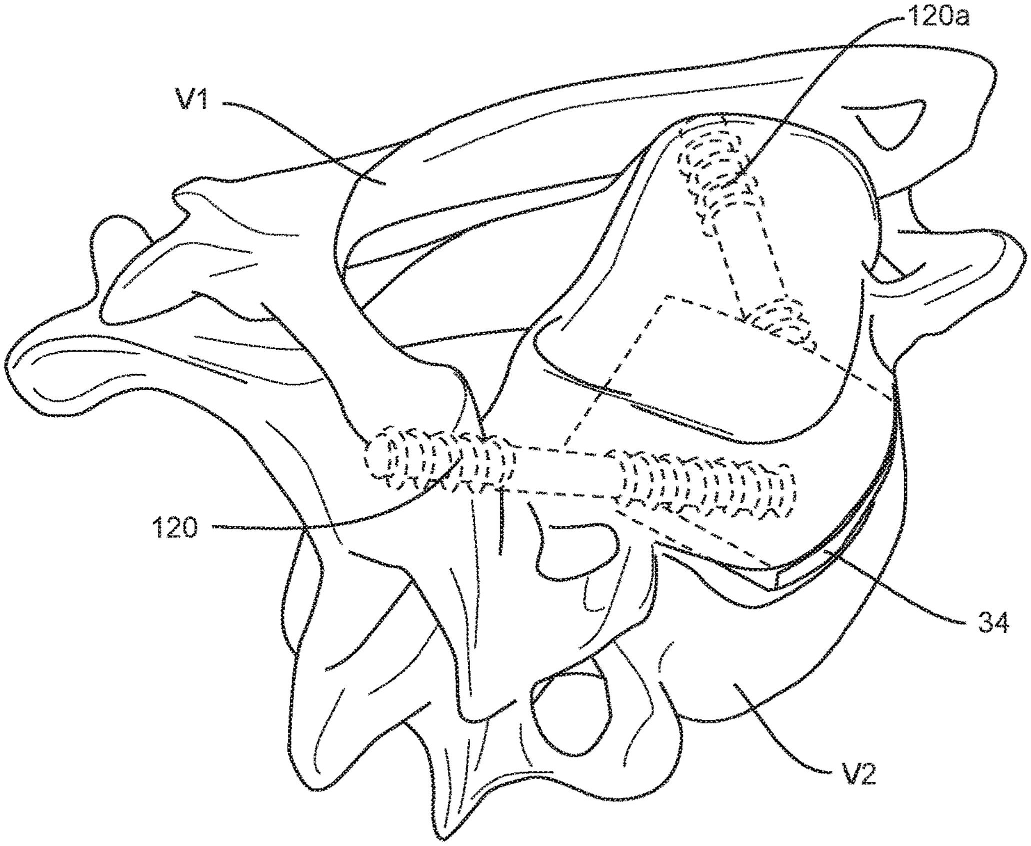
FIG. 12 is a perspective view of components of one embodiment of a spinal implant in accordance with the principles of the present disclosure disposed with vertebrae.
Figure 13:
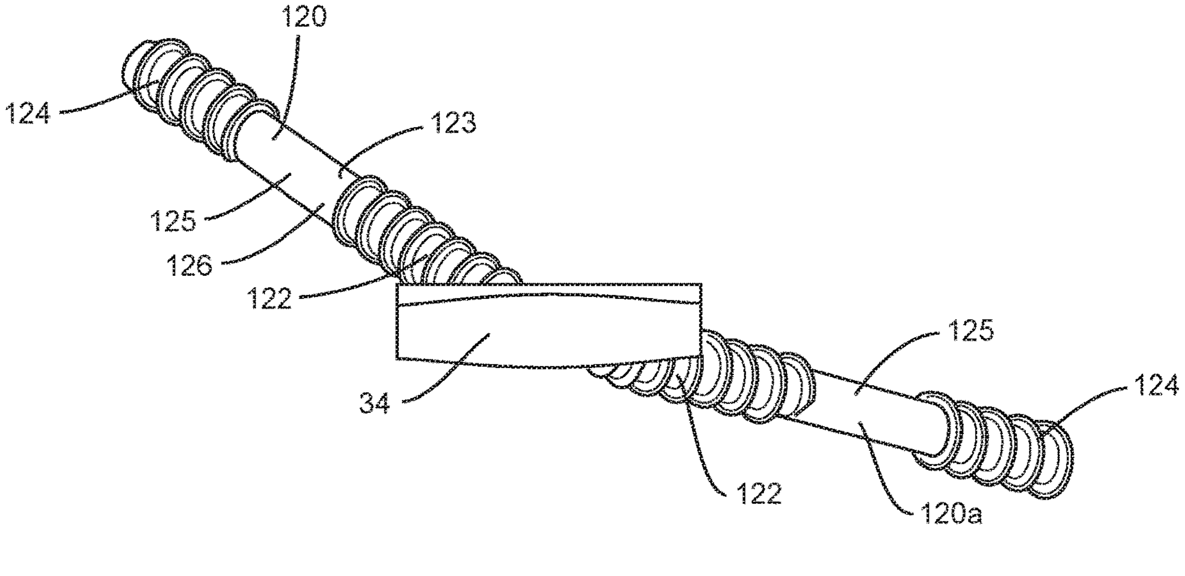
FIG. 13 is a side view of the components and vertebrae shown in FIG. 12.
Figure 14:
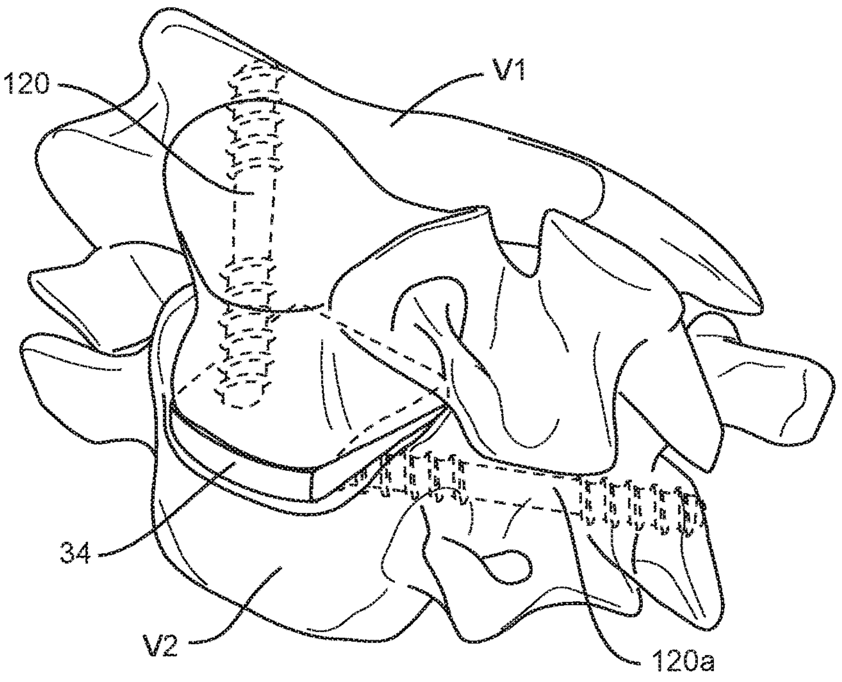
FIG. 14 is a perspective view of the components and vertebrae shown in FIG. 12.
Figure 15:
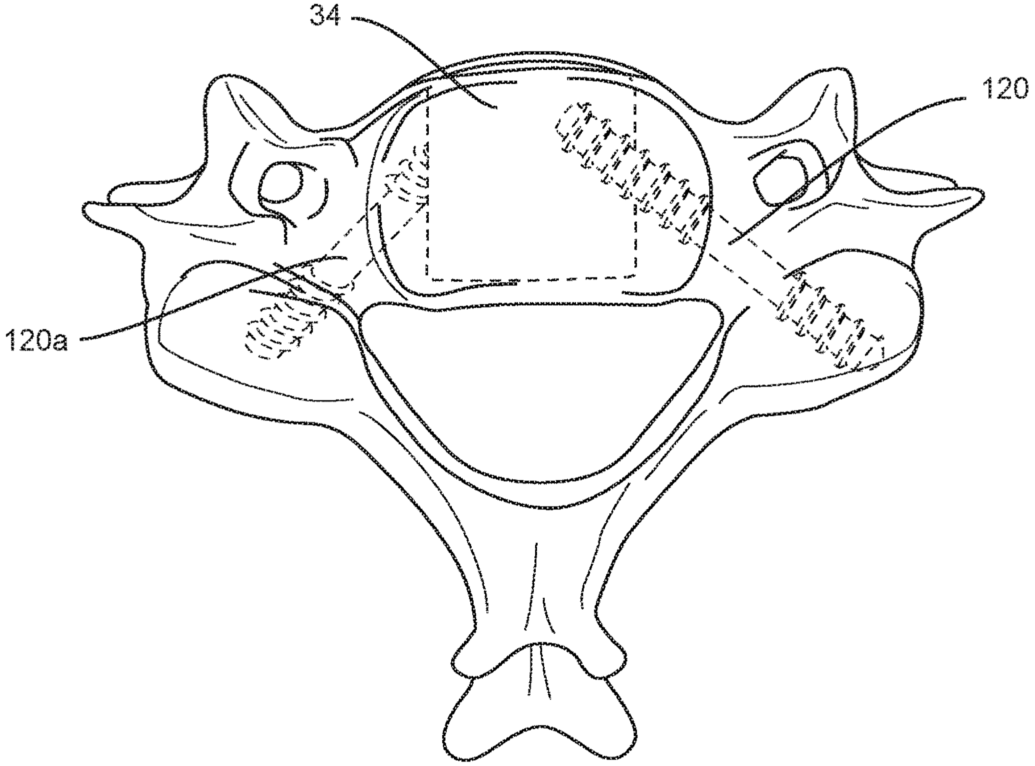
FIG. 15 is a plan view of the components and vertebrae shown in FIG. 12.

As shown in FIGS. 13 and 14, bone fastener 120 includes two bone fasteners 120 and 120*a*. Bone fastener 120 is configured for fixation with vertebra V1 and bone fastener 120*a* is configured for fixation with a vertebra V2. In some embodiments, bone fasteners 120, 120*a* are configured for delivery via a divergent trajectory. In some embodiments, bone fasteners 120, 120*a* are configured for delivery via a convergent trajectory. In some embodiments, bone fasteners 120, 120*a* are configured for delivery via a crossing trajectory. Bone fasteners 120, 120*a* are configured for engagement with interbody device 34, as shown in FIGS. 12-14.

Figure 16:
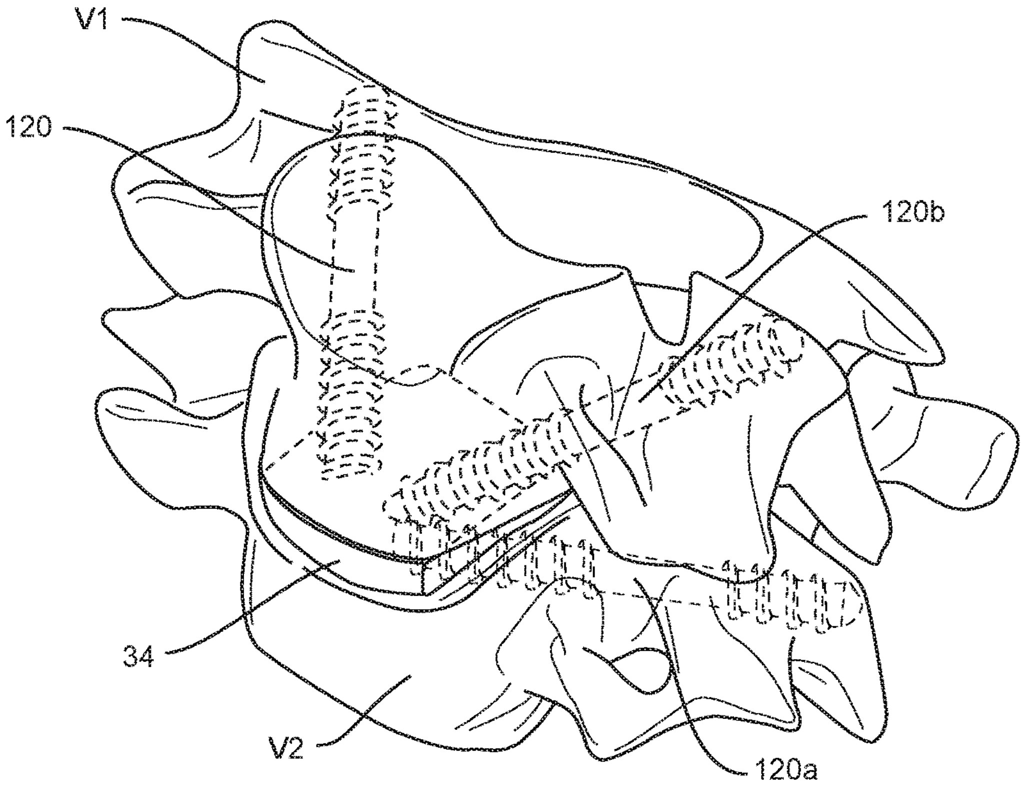
FIG. 16 is a perspective view of components of one embodiment of a spinal implant in accordance with the principles of the present disclosure disposed with vertebrae.
Figure 17:
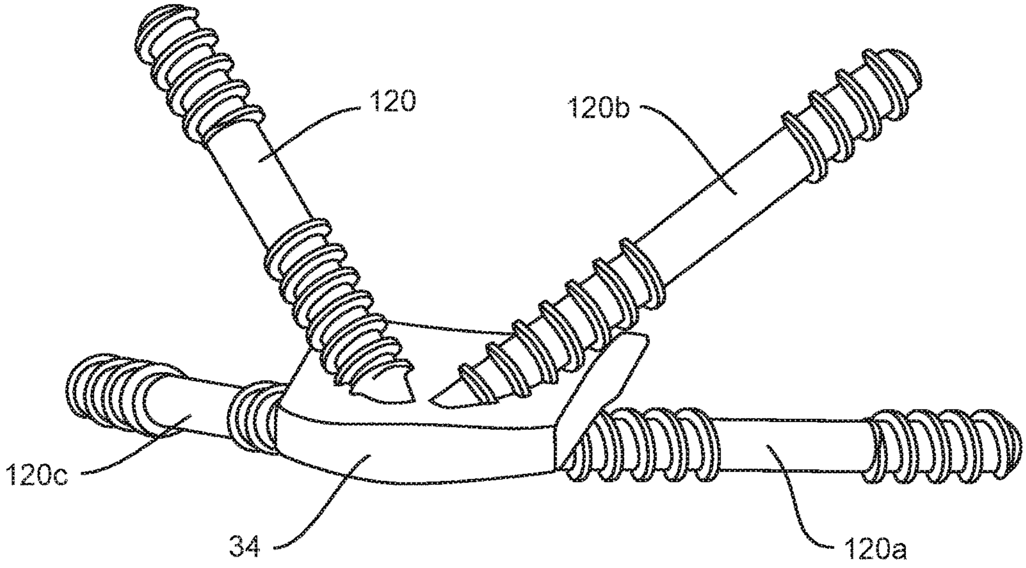
FIG. 17 is a perspective view of the components shown in FIG. 16.

In one embodiment, as shown in FIGS. 16-17, spinal implant system 10, similar to the systems and methods described with regard to FIGS. 12-15, includes bone fasteners 120, 120*a*, and bone fasteners 120*b* and 120*c* similar to bone fastener 120. Bone fasteners 120, 120*a*, 120*b* and 120*c* are configured for engagement with openings 44 of interbody device 34. Bone fasteners 120, **120*b* are configured for fixation with vertebra V1 and bone fasteners 120*a*, 120*c* are configured for fixation with vertebra V2, as shown in FIG. 16**.

Figure 18:
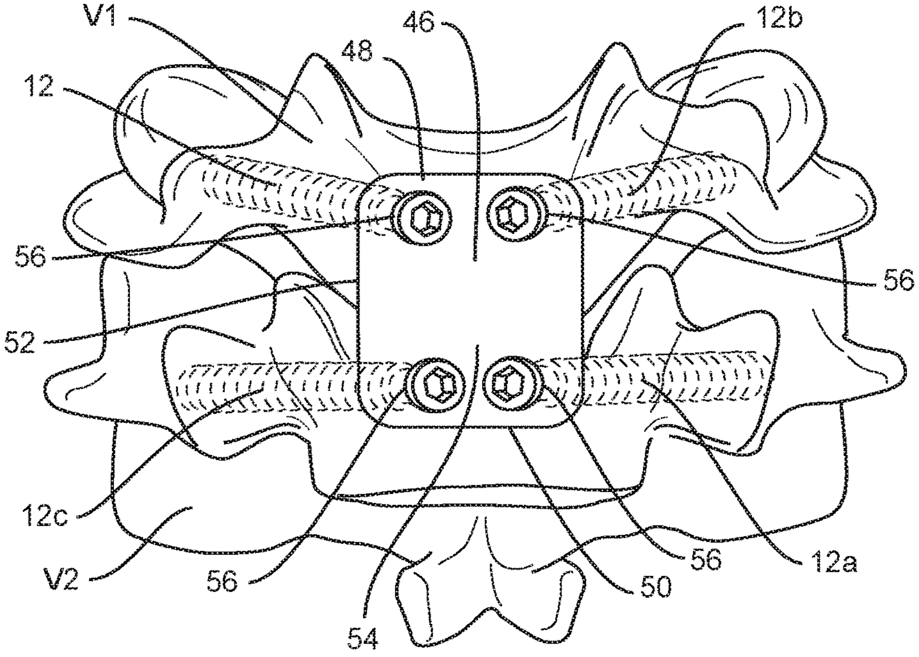
FIG. 18 is a plan view of components of one embodiment of a spinal implant in accordance with the principles of the present disclosure disposed with vertebrae.
Figure 19:
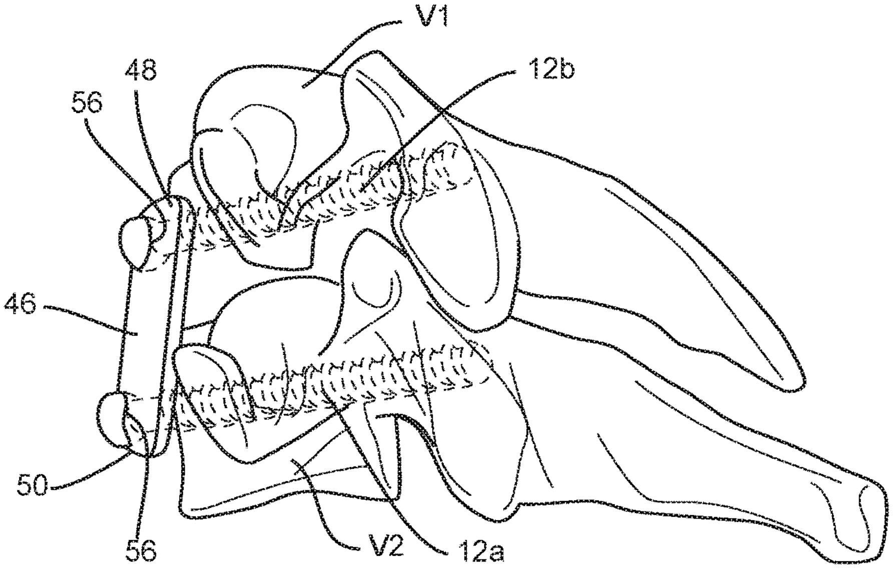
FIG. 19 is a side view of the components and vertebrae shown in FIG. 18.
Figure 20:
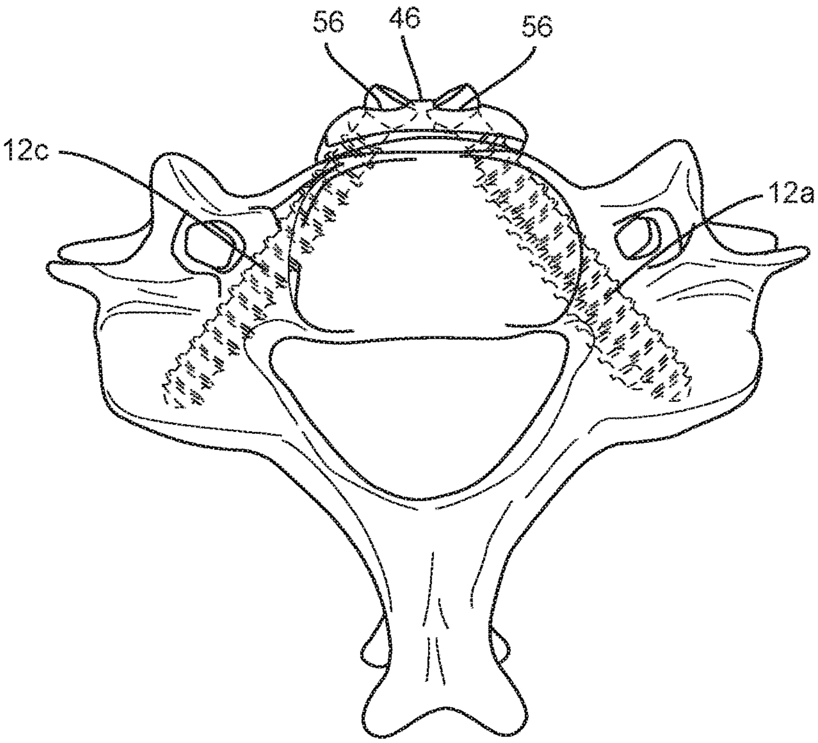
FIG. 20 is a plan view of the components and vertebrae shown in FIG. 18.

In one embodiment, as shown in FIGS. 18-20, spinal implant system 10, similar to the systems and methods described with regard to FIGS. 1-17, includes a plate, for example, an anterior cervical plate 46. In some embodiments, plate 46 is used alternatively or in addition to interbody device 34. Plate 46 includes a single level configuration for connecting two vertebral bodies, for example, vertebrae V1 and V2, extending along a single intervertebral disc space, as shown in FIG. 18. Plate 46 has a substantially rectangular shape. In some embodiments, plate 46 is variously shaped, such as, for example, oblong, oval, triangular, polygonal, irregular, uniform, non-uniform, variable and/or tapered.

Plate 46 extends between an end 48 and an end 50. In some embodiments, multiple single level plates 46 are utilized to move with selected vertebrae independently, and provide load sharing, facilitate fusion and avoid imbalance on the individual disc levels. For example, a load applied to vertebrae is transferred to each plate 46 separately to facilitate the independent movement to enhance fusion and maintain balance. In some embodiments, multiple single level plates 46 are disposed in a serial orientation along selected vertebra. In some embodiments, multiple single level plates 46 having one or more configurations and dimensions are stacked in a selected orientation along selected vertebra.

Plate 46 includes a wall 52 that extends between ends 48, 50. Plate 46 includes a surface 54 configured for engagement with a surface of vertebrae V1 and V2. In some embodiments, surface 54 may have various surface configurations, such as, for example, rough, threaded, arcuate, undulating, porous, semi-porous, dimpled, polished and/or textured.

Surface 54 defines openings 56 configured for disposal of bone fasteners 12, **12*a*, 12*b* and 12*c*, as shown in FIG. 18. Openings 56 are circular. In some embodiments, openings 56 may be disposed at alternate orientations, relative to wall 52 and/or surface 54, such as, for example, substantially transverse, perpendicular, parallel and/or other angular orientations such as acute or obtuse, and/or may be offset. In some embodiments, openings 56 can be variously configured, such as, for example, oval, oblong, triangular, square, polygonal, irregular, uniform, non-uniform, tapered and/or countersunk. In some embodiments, plate 46 can have one or a plurality of openings 26. In some embodiments, bone fasteners 12, 12*a*, 12*b* and 12*c* are disposed within openings 56 of plate 46 and are oriented along an anterior trajectory that passes through a first cortical surface or layer, for example, the CAS of vertebra V1 above or below where the disc has been removed by the discectomy. Bone fasteners 12, 12*a*, 12*b* and 12*c* then pass through cancellous bone of vertebra V1 and into or through a second cortical surface or layer, for example, the CS of vertebra V1 and/or a pedicle of vertebra V1. In some embodiments, bone fasteners 12, 12*a*, 12*b* and 12*c* will stop within the pedicle or pass through a posterior cortical surface and/or layer of vertebra V1**.

Figure 21:
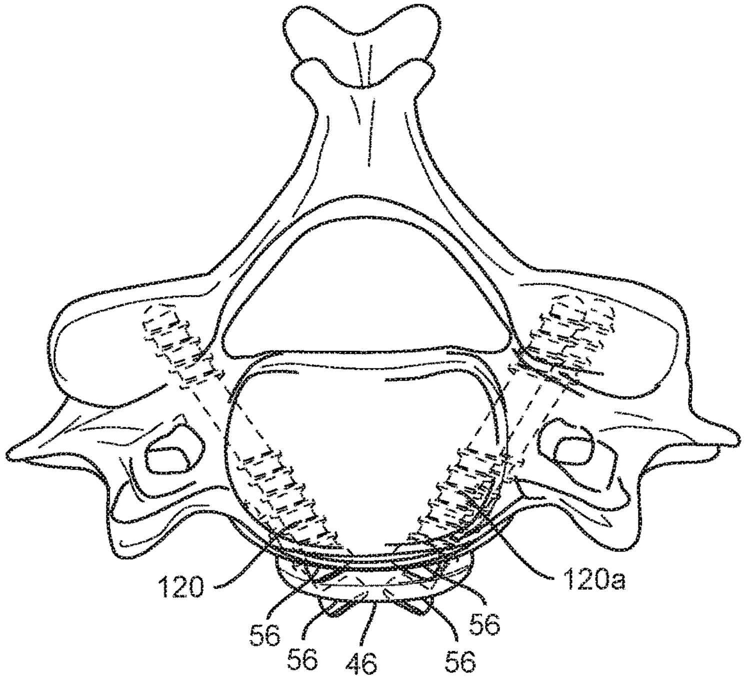
FIG. 21 is a plan view of components of one embodiment of a spinal implant in accordance with the principles of the present disclosure disposed with vertebrae.
Figure 22:
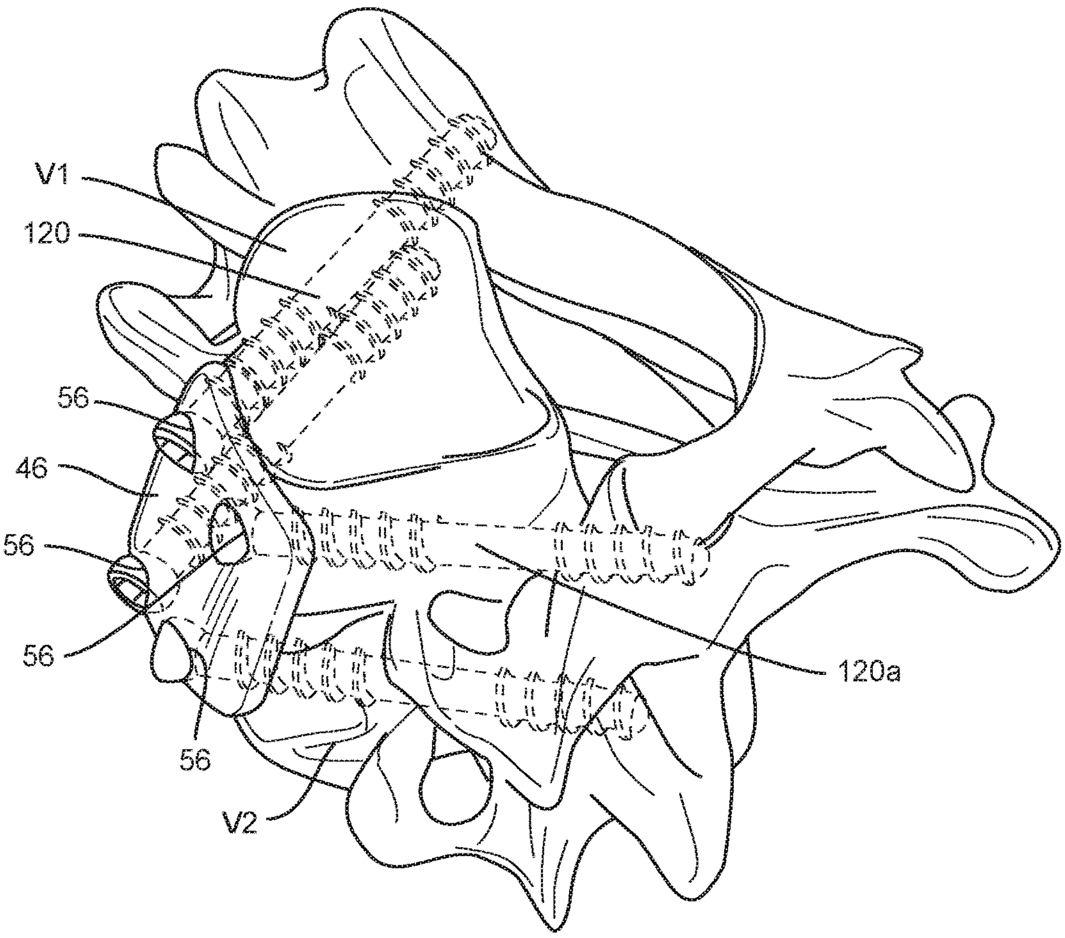
FIG. 22 is a perspective view of the components and vertebrae shown in FIG. 21.

In one embodiment, as shown in FIGS. 21-22, spinal implant system 10, similar to the systems and methods described with regard to FIGS. 18-20, includes bone fasteners 120, **120*a*, 120*b* and 120*c* implemented with plate 46. In some embodiments, a combination of bone fasteners 12 and bone fasteners 120 can be implemented with plate 46**.

In one embodiment, as shown in FIGS. 23-26, spinal implant system 10, similar to the systems and methods described with regard to FIGS. 1-7, includes a bone fastener 220, similar to bone fastener 12. Bone fastener 220 includes a proximal portion 222 including a head 223, and a distal portion 224. A shaft 230 is disposed between portions 222, 224 and includes an outer threaded surface 226. Portions 222, 224 are configured for bi-cortical fixation with the cortical surfaces of vertebrae V1, as described herein.

Figure 23:
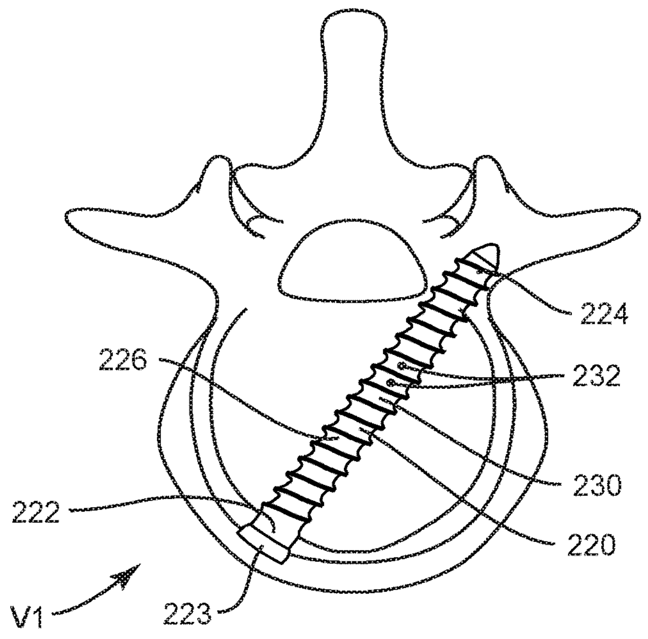
FIG. 23 is a plan view of components of one embodiment of a spinal implant in accordance with the principles of the present disclosure disposed with vertebrae.
Figure 24:
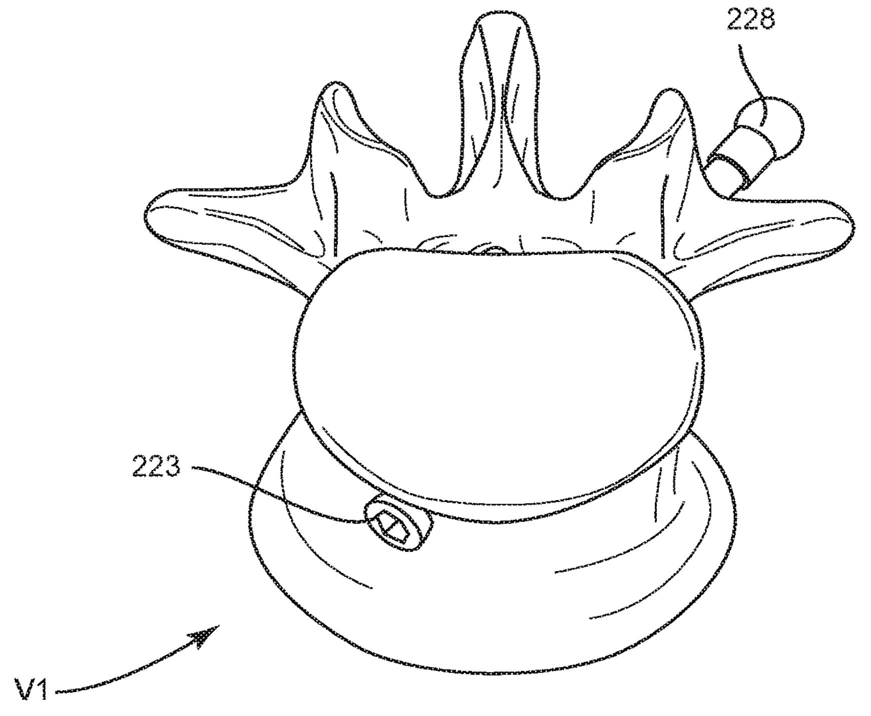
FIG. 24 is a perspective view of the components and vertebrae shown in FIG. 23.
Figure 25:
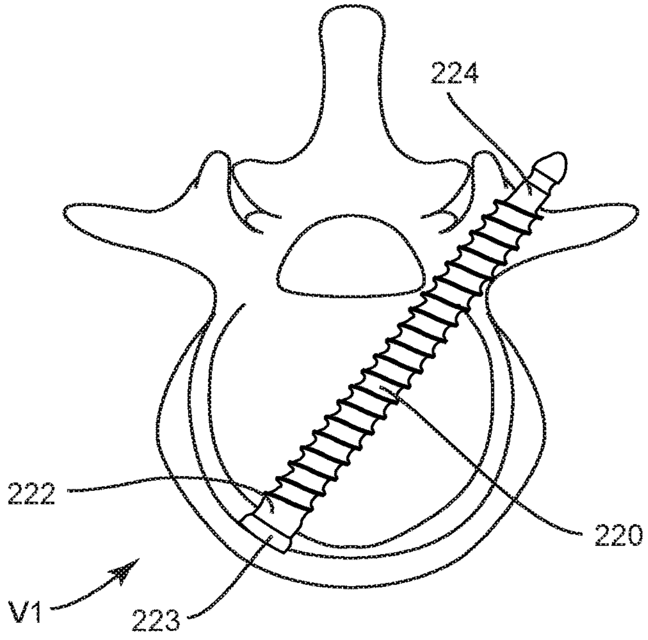
FIG. 25 is a perspective view of the components and vertebrae shown in FIG. 23.
Figure 26:
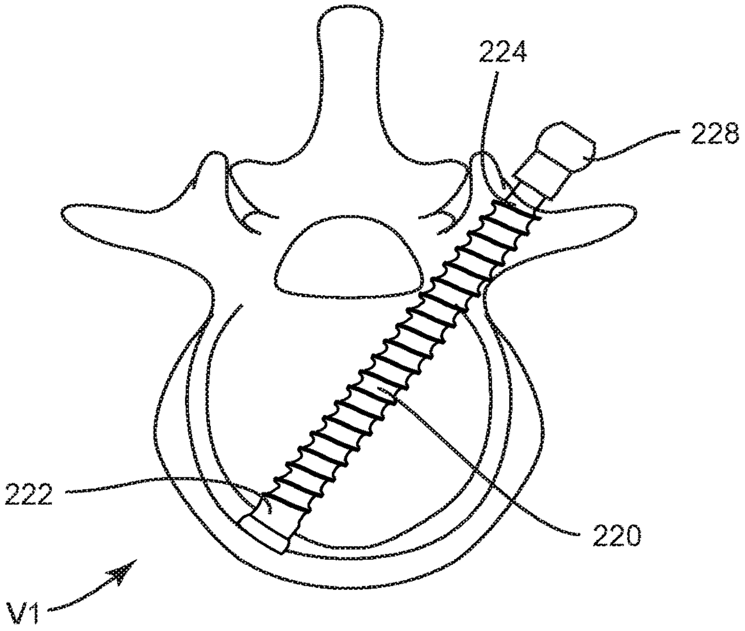
FIG. 26 is a perspective view of the components and vertebra shown in FIG. 23.

In some embodiments, spinal implant system 10 includes a posterior implant, for example, a head 228 and/or a cap configured for manual engagement with shaft 230 at portion 224, as shown in FIGS. 23 and 24. In some embodiments, portion 224 is manually engaged in a pop-on or snap-on engagement with head 228. Head 228 is configured to provide increased fixation to bone fastener 220 and is configured for engagement with a surface of vertebra V1, for example, a surface of the pedicle. In some embodiments, head 228 includes a MAS head. In some embodiments, portion 224 includes a mating surface that includes, for example, one or more ridges or recesses, which engage with a mating surface that includes, for example, one or more ridges or recesses of head 228 to improve purchase of head 228 with portion 224. In some embodiments, portion 224 includes a detachable burred tip (not shown) to facilitate implantation of bone fastener 220. In some embodiments, the burred tip is disconnected after bone fastener 220 implantation and head 228 manually engages with portion 224. In some embodiments, the posterior implant can include one or more spinal rods connected with portion 224 via receivers and/or set screws.

As shown in FIG. 23, shaft 230 is cannulated and includes one or a plurality of openings, for example, fenestrations 232. In some embodiments, fenestrations 232 are configured to deliver an agent, for example, a cement. In some embodiments, an agent source is connected to portion 222 of bone fastener 220 for communication with fenestrations 232 via the cannulated shaft 230 and delivery therefrom. In some embodiments, fenestrations 232 extend only up to a midline length or half the length of shaft 230. Fenestrations 232 are circular. In some embodiments, fenestrations 232 can be variously configured, such as, for example, oval, oblong, triangular, square, polygonal, irregular, uniform, non-uniform, tapered and/or countersunk.

Figure 27:
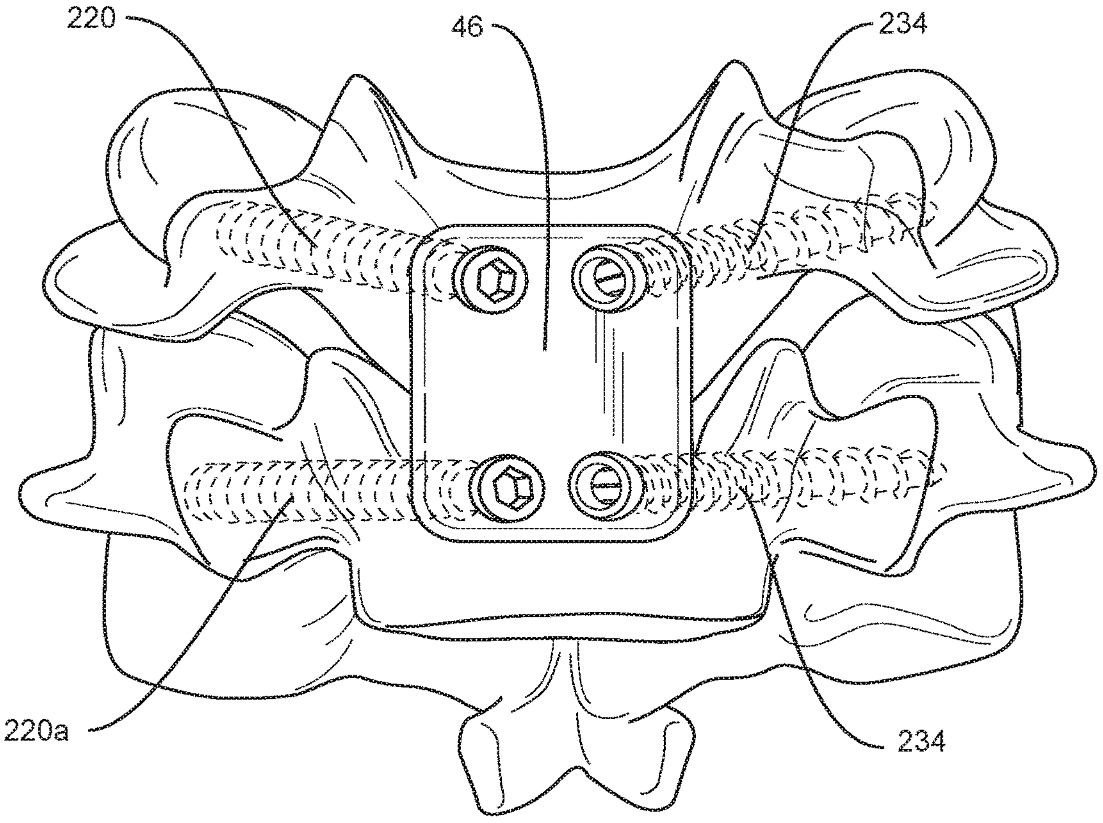
FIG. 27 is a plan view of components of one embodiment of a spinal implant in accordance with the principles of the present disclosure disposed with vertebrae.

In one embodiment, as shown in FIG. 27, spinal implant system 10, similar to the systems and methods described with regard to FIGS. 23-26, includes one or more bone fasteners 220 implemented with plate 46. In some embodiments, one or more bone fasteners 220 and one or more archetypal anterior bone fasteners 234 can be implemented with plate 46. In some embodiments, one side of plate 46 can employ two bone fasteners 220, **220*a* and on an opposing side, plate 46 can employ two archetypal anterior bone fasteners 234 to affix plate 46. In some embodiments, plate 46 can be affixed from an oblique approach. In some embodiments, plate 46** can be affixed from an oblique lateral lumbar interbody fusion (OLIF) approach.

In some embodiments, one or more spinal implants of spinal implant system 10, may be engaged with tissue in various orientations, for example, series, parallel, offset, staggered and/or alternate vertebral levels. In some embodiments, the spinal implant of spinal implant system 10 may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, spinal implant system 10 includes an agent, which may be disposed, packed, coated or layered within, on or about the components and/or surfaces of spinal implant system 10. In some embodiments, the agent may include bone growth promoting material, for example, bone cement or bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:

at least one plate including a first end and a second end, the plate including a first opening at the first end and a second opening at the second end; and at least one first bone fastener extending through the first opening and at least one second bone fastener extending through the second opening, each bone fastener including a proximal portion and a distal portion, the proximal portion being engageable with a surgical driver having a surgical navigation component that generates data for display of an image representing position of the spinal implant relative to the vertebra, the proximal portion of the first bone fastener being fixable with an anterior cortical surface of a cephalad cervical vertebra such that the proximal portion of the first bone fastener secures the plate to the anterior cortical surface of the cephalad cervical vertebra and the distal portion of the first bone fastener being fixable with a cortical surface of a pedicle of the cephalad cervical vertebra, the proximal portion of the second bone fastener being fixable with an anterior cortical surface of a caudal cervical vertebra such that the proximal portion of the second bone fastener secures the plate to the anterior cortical surface of the caudal cervical vertebra and the distal portion of the second bone fastener being fixable with a cortical surface of a pedicle of the caudal cervical vertebra.

2. A spinal implant as recited in claim 1, wherein the first anterior cortical surface is spaced apart from the second cortical surface for bi-cortical fixation.

3. A spinal implant as recited in claim 1, wherein the at least one first bone fastener includes a first cephalad bone fastener and a second cephalad bone fastener extending from the first end, and the at least one second bone fastener includes a first caudal bone fastener and a second caudal bone fastener extending from the second end.

4. A spinal implant as recited in claim 1, wherein at least one of the bone fasteners is threaded entirely from the proximal portion to the distal portion.

5. A spinal implant as recited in claim 1, wherein at least one of the bone fasteners is threaded at the proximal portion and the distal portion for fixation with the cortical surfaces and is non-threaded at an intermediate portion.

6. A spinal implant as recited in claim 1, wherein at least one of the bone fasteners includes a cannulated shaft having at least one fenestration configured for delivery of a cement to the vertebra.

7. A spinal implant as recited in claim 1, wherein the distal portion includes a mating surface engageable with a mating surface of a pop-on head.

8. A spinal implant system according to claim 1, wherein the at least one first bone fastener and the at least one second bone fastener are delivered via divergent anterior pedicle trajectories.

9. A spinal implant as recited in claim 1, wherein the at least one plate includes a plurality of plates disposed in a selected orientation with the vertebrae.

10. A spinal implant as recited in claim 1, wherein the spinal implant includes an interbody device configured for engagement with the vertebrae and at least one of the bone fasteners.

11. A spinal implant system comprising:

a spinal implant including at least one plate including a first end and a second end, the plate including a first opening at the first end and a second opening at the second end, at least one cephalad bone fastener extending through the first opening and including a proximal portion and a distal portion, and at least one caudal bone fastener extending through the second opening and including a proximal portion and a distal portion; and a surgical driver engageable with the bone fasteners for delivery from an anterior trajectory, the surgical driver includes a surgical navigation component that communicates with a tracking device including a sensor that receives a signal and communicates with a processor to generate data for display of an image from a monitor, the image representing position of the spinal implant relative to one or more cervical vertebra, the proximal portion of the at least one cephalad bone fastener being fixable with a first anterior cortical surface of a cephalad cervical vertebra such that the proximal portion of the at least one cephalad bone fastener secures the plate to the first anterior cortical surface and the distal portion of the at least one cephalad bone fastener being fixable with a cortical surface of a pedicle of the cephalad cervical vertebra, the proximal portion of the at least one caudal bone fastener being fixable with a second anterior cortical surface of a caudal cervical vertebra such that the proximal portion of the at least one caudal bone fastener secures the plate to the second anterior cortical surface and the distal portion of the at least one caudal bone fastener being fixable with a cortical surface of a pedicle of the caudal cervical vertebra.

12. A spinal implant system according to claim 11, wherein the first cortical surface is an anterior surface that is spaced apart from the second cortical surface for bi-cortical fixation.

13. A spinal implant system according to claim 11, wherein at least one of the bone fasteners is threaded at the proximal portion and the distal portion for fixation with the cortical surfaces and is non-threaded at an intermediate portion.

14. A spinal implant system according to claim 11, wherein the at least one cephalad bone fastener includes a first bone fastener and a second bone fastener extending from the first end, and the at least one caudal bone fastener includes a first bone fastener and a caudal bone fastener extending from the second end.

15. A spinal implant system according to claim 11, wherein the spinal implant system further comprises a posterior implant connected with the distal portion.

16. A spinal implant system according to claim 11, wherein the surgical driver is connected to a guide member having an end effector of a robotic arm.

17. A method for treating a spine, the method comprising the steps of:

selecting a pathway from an anterior approach that includes cervical vertebrae;

creating a cavity in an anterior cortical surface of a cephalad cervical vertebra and a cavity in a cortical surface of a pedicle of the cephalad cervical vertebra, the cavities being created along the pathway via surgical navigation;

creating a cavity in an anterior cortical surface of a caudal cervical vertebra and a cavity in a cortical surface of a pedicle of the caudal cervical vertebra, the cavities being created along the pathway via surgical navigation;

delivering a spinal implant including a plate including a first end and a second end, the plate including a first opening at the first end and a second opening at the second end, at least one first bone fastener extending through the first opening and at least one second bone fastener extending through the second opening along the pathway via surgical navigation, each of the bone fasteners including a proximal portion and a distal portion;

fixing the proximal portion of the first bone fastener with an anterior cortical surface of a cephalad cervical vertebra such that the proximal portion of the first bone fastener secures the plate to the anterior cortical surface of the cephalad cervical vertebra and fixing the distal portion of the first bone fastener with a cortical surface of a pedicle of the cephalad cervical vertebra; and fixing the proximal portion of the second bone fastener with an anterior cortical surface of a caudal cervical vertebra such that the proximal portion of the second bone fastener secures the plate to the anterior cortical surface of the caudal cervical vertebra and fixing the distal portion of the second bone fastener with a cortical surface of a pedicle of the caudal cervical vertebra such that the first bone fastener and the second bone fastener are disposed along divergent anterior pedicle trajectories with the cervical vertebrae, and the cortical surfaces are spaced apart for bi-cortical fixation.

18. A method as recited in claim 17, wherein the step of delivering includes engaging a surgically navigated driver with the implant, and the surgical navigation communicates with a tracking device including a sensor that receives a signal and communicates with a processor to generate data for display of an image from a monitor, the image representing position of the spinal implant relative to the cervical vertebra.

19. A method as recited in claim 17, wherein the at least one first bone fastener includes a first cephalad bone fastener and a second cephalad bone fastener extending from the first end, and the at least one second bone fastener includes a first caudal bone fastener and a second caudal bone fastener extending from the second end.

20. A method as recited in claim 17, wherein the spinal implant includes an interbody device configured for engagement with the cervical vertebra and at least one of the bone fasteners.

* * * * *